United States Patent
Tian et al.

(10) Patent No.: US 11,197,799 B2
(45) Date of Patent: Dec. 14, 2021

(54) SYSTEM AND METHOD FOR GENERATING PRESSURE POINT MAPS BASED ON REMOTE-CONTROLLED HAPTIC-INTERACTIONS

(71) Applicant: MIDEA GROUP CO., LTD., Foshan (CN)

(72) Inventors: Yuan Tian, San Jose, CA (US); Suresh Mani, San Jose, CA (US)

(73) Assignee: MIDEA GROUP CO., LTD., Foshan (CN)

( * ) Notice: Subject to any disclaimer, the term of this patent is extended or adjusted under 35 U.S.C. 154(b) by 447 days.

(21) Appl. No.: 16/351,334

(22) Filed: Mar. 12, 2019

(65) Prior Publication Data

US 2020/0121556 A1     Apr. 23, 2020

Related U.S. Application Data

(60) Provisional application No. 62/747,065, filed on Oct. 17, 2018.

(51) Int. Cl.
*A61H 39/02*     (2006.01)
*B25J 9/16*     (2006.01)
(Continued)

(52) U.S. Cl.
CPC .......... *A61H 39/02* (2013.01); *B25J 9/1664* (2013.01); *G05B 15/02* (2013.01);
(Continued)

(58) Field of Classification Search
CPC ............. A61H 39/02; A61H 2201/501; A61H 2201/1659; A61H 2203/0443; A61H 2230/425; A61H 2230/625; A61H 2201/5097; A61H 2230/505; A61H 2201/5071; A61H 15/00; A61H 39/04; A61H 2201/5058; A61H 2230/305; A61H 2201/10; A61H 2201/1669; A61H 2201/0196; A61H 2201/5082;
(Continued)

(56) References Cited

U.S. PATENT DOCUMENTS

2019/0343717 A1*   11/2019   Yim ..................... A61B 5/4854

\* cited by examiner

*Primary Examiner* — Eugene T Wu
(74) *Attorney, Agent, or Firm* — Morgan, Lewis & Bockius LLP

(57) ABSTRACT

System and method for providing remotely guided physical treatment are disclosed. A computing device is communicably coupled to a therapeutic robot and a remote guidance device. The computing device receives full-body images of a treatment subject. The computing device generates a plurality of key physical points for the treatment subject by identifying a three-dimensional human body template that corresponds to the shape and posture parameters of the treatment subject and fitting the identified first three-dimensional human body template to the full-body images of the treatment subject. The fitting causes adjustments to locations of the corresponding set of key physical points of the first three-dimensional human body template. The adjusted locations of the corresponding set of key physical points of the first three-dimensional human body template are provided to the guidance device as basis for a treatment procedure that is specified by the treatment guidance provider during the physical treatment session.

17 Claims, 11 Drawing Sheets

(51) Int. Cl.
*G05B 15/02* (2006.01)
*A61B 34/10* (2016.01)
(52) U.S. Cl.
CPC .................. *A61B 2034/107* (2016.02); *A61H 2201/1659* (2013.01); *A61H 2201/501* (2013.01)
(58) Field of Classification Search
CPC ......... A61H 2230/605; A61H 2230/065; B25J 9/1664; G05B 15/02; A61B 2034/107
See application file for complete search history.

600

602 At a computing device having one or more processors and memory, wherein the computing device is communicably coupled to a therapeutic robot, and to a guidance device including a first display generation component and a first input device, and wherein the therapeutic robot is collocated with a treatment subject and the guidance device is collocated with a treatment guidance provider during a physical treatment session:

604 Receiving one or more full-body images of the treatment subject

606 Generating a plurality of key physical points for the treatment subject, including:

608 Determining a plurality of shape parameters and posture parameters of the treatment subject from the one or more full-body images of the treatment subject 610 Identifying a first three-dimensional human body template that corresponds to the plurality of shape parameters and posture parameters of the treatment subject, wherein the first three-dimensional human body template has a corresponding set of key physical points 612 Fitting the identified first three-dimensional human body template to the one or more full-body images of the treatment subject, wherein the fitting causes adjustments to locations of at least one of the corresponding set of key physical points of the first three-dimensional human body template

614 Providing the adjusted locations of the corresponding set of key physical points of the first three-dimensional human body template to the guidance device, wherein the adjusted locations of the corresponding set of key physical points of the first three-dimensional human body template provides a basis for a treatment procedure that is specified by the treatment guidance provider during the physical treatment session

Figure 6

SYSTEM AND METHOD FOR GENERATING PRESSURE POINT MAPS BASED ON REMOTE-CONTROLLED HAPTIC-INTERACTIONS

RELATED APPLICATION

This application claims the benefit of U.S. Provisional Patent Application No. 62/747,065, filed Oct. 17, 2018, the content of which is incorporated herein in its entirety.

TECHNICAL FIELD

This relates generally to therapeutic technologies, including but not limited to providing remotely-guided acupuncture and therapeutic physical manipulations to human patients.

BACKGROUND

Today, physical therapy that involves acupuncture treatments, pressure point therapy, deep tissue massages, targeted heat treatments, targeted ice treatment, target electric muscle stimulation therapies, etc. are widely adopted and used. A common element in these different types of treatments is that they all involve targeted actions (e.g., insertion of acupuncture needles, application of electric pulses, application of heating, ice pack, and/or pressure, etc.) performed in accordance with specific locations on a patient's body (e.g., pressure points, acupuncture points (Xue Wei), trigger points, knots, cramp/spasm sites, joints, etc.) that are identified by treatment personnel. A patient typically gets evaluated in person by a physical therapist, massage therapist, a traditional oriental medicine doctor, a personal trainer, or some other experts that are skilled at identifying the problems that the patient has with his/her muscles, joints, body, health and/or wellbeing, determining suitable treatment procedures, and determining suitable locations on the body that should be treated with the identified treatment procedures. The therapy itself requires the treatment personnel to physically perform the procedures on the patient's body, to help the patient achieve relaxation, pain reduction, reduction of physical symptoms, improving circulation, healing of injuries, and ultimately improved health and/or wellbeing for the patient.

There are multiple issues with the above treatment practices. First, it requires many years of studying and practicing to achieve the skill level of a trained practitioner in the field of physical medicine. The lack of qualified teachers and institutions overall in this field make it difficult to spread the knowledge and expertise in this very rich and diverse field. In addition, the practices require not only mental acuity and talent, but also physical skills that take much practice to develop. Many patients do not want to become the subject of a novice practitioner, and as a result, it takes much longer for a novice to become a skilled practitioner. A lot of the treatment procedures performed by the practitioners require not only knowledge and skill, but also physical strength and stamina. A lot of skilled and experienced practitioner cannot continue to practice effectively because they are advanced in years and are easily fatigued due to the physical demand of the practice.

Other aspects of physical therapy may prevent it from becoming as widely utilized includes privacy concerns, hygienic concerns, and time/space limitations. For example, some patients are reluctant to try out treatments involving physical manipulations because they are uncomfortable with the extent of physical contact and/or close physical proximity of the therapist, or remaining undressed for an extended period of time during the treatment process. Some people are uncomfortable with going to a facility where massage tables and equipment have been shared with other patients. Sometimes, a well-regarded treatment facility may be overbooked, or have unreasonably long wait-times.

Although there have been some attempts at addressing some of the issues outlined above. The solutions are far from adequate. For example, automatic massage chairs can be used to perform massages in accordance with a few preset programs targeting various locations of the body (e.g., back, legs, shoulders, etc.) or having predefined goals (e.g., relaxing muscles, reducing back pain, improving circulation, etc.). However, the massage chair and the preset programs are not tailored to individual patients, and do not work well for many patients (e.g., due to variations in size, height, symptoms, injuries, etc.). Handheld massage devices or electric muscle stimulation devices allow patients to self-direct the device to the locations on his/her bodies that need treatment. However, due to the lack of skills and diminished physical capabilities due to age, pain, and injuries on the part of the patients, the effectiveness of the self-help devices are low as well. Videos and self-help books on self-administered and armature-administered treatment may help in some low-risk scenarios, but pose increased problems and harm to the patients for more complex treatment scenarios. Although one may contemplate remotely controlling a message device to treat a patient, real research and development on this front is very limited to date.

It is challenging to provide an effective and efficient human-machine interface that facilitates remotely-guided acupuncture and therapeutic physical manipulations. Good techniques for supporting expert guidance, and indirect and/or intermittent expert intervention during remotely-guided physical therapeutic treatment of a patient (e.g., by a local operator, or a robot) in real-time over a network are in great need.

SUMMARY

Accordingly, there is a great need for an effective and efficient human-machine interface that facilitates remotely-guided acupuncture and therapeutic physical manipulations, and for good techniques for supporting expert guidance, and indirect and/or intermittent expert intervention during remotely-guided physical therapeutic treatment of a patient (e.g., by a local operator, or a robot).

In this disclosure, a treatment environment includes a local site (e.g., local site 102 as shown in FIG. 1A) and a remote site (e.g., remote site 105 as shown in FIG. 1B). A patient is located at the local site with a therapeutic robot and/or a local human treatment operator. RGBD images of the patient streamed from the local site is provided to a central computer (e.g., central computing system 120 in FIGS. 1A and 2B) which processes the images and generates three-dimensional (or pseudo-3D models) of the patient's body in real-time, and corresponding locations of key physical points (e.g., joints, muscles, acupuncture points, trigger points, pressure points, etc.) for the patient's body. The three-dimensional images and corresponding locations for the key physical points are continuously updated and tracked in real-time during a treatment session, such that the treatment can be administered to the correct locations on the patient's body throughout the treatment session, even when the patient has moved its body and/or changed his/her posture (e.g., due to application of force, sensitivity or discomfort caused by the treatment, and/or fatigue caused by a fixed posture, etc.). The central computer includes a template model that is trained on expert-annotated 3D images (or pseudo-3D images) of human subjects that include human bodies of different shapes, sizes, ages, genders, races, etc. in different postures, and the annotation includes locations of key physical points (e.g., joints, muscles, acupuncture points, trigger points, pressure points, etc.) on each of the images. The central computer also includes a fitting tracking model that continues to track the locations of the key physical points when consecutive frames of images of the same patient is streamed and processed.

In some embodiments, the three-dimensional model (or a sub-portion thereof) of a patient at the local site is transmitted back to the local site and presented at the local site with the key physical points (or a selected subset thereof) overlaid on top. The locally presented patient model and overlaid key physical points help provide guidance on the exact location(s) of treatment for the patient. A patient or a local treatment operator can perform the treatment to the identified location(s) in accordance with the guidance provided in the locally presented images. This allows less skilled personnel or the patient himself to administer the treatment, reducing the demand on highly skilled practitioners to be physically present at the patient's site to administer the treatment. This is also more effective than administering the treatment based on online demo videos or text books, because the key physical points are identified for the patient's particular body and posture, and are updated in real-time to maintain accuracy of the locations. For certain areas of the body or certain types of lower risk treatment, the patient or his/her caregiver can perform the treatment at the patient's home with better privacy and convenience to the patient.

In some embodiments, in addition to the local site, the treatment environment includes a remote site, where a mixed reality environment is utilized for a remote expert to perceive the 3D model of the patient's body (e.g., through point cloud images or other 3D rendering of the patient's body, and haptic feedback provided on a haptic input device) and provide treatment guidance inputs (e.g., verbal instructions, haptic movement demonstration instructions, etc.) as needed. At the remote site, the patient's 3D model is displayed overlaid with the key physical points that have been identified by the central computer. The remote expert can adjust the locations of the automatically identified key physical points on the display (e.g., using the user interface 500 shown in FIG. 5) based on his own personal expertise, and/or select a subset of them for particular treatment procedures. The remote expert can provide high-level instructions to the patient and/or the local treatment operator to execute the treatment procedures to one or more regions of the patient's body in sequence. In accordance with this remote expert-facilitated mixed-reality setup, the remote expert can help monitor and guide the treatment of multiple patients respectively located at multiple different locations at the same time. The remote expert can be relieved from the physically demanding and strenuous tasks of manually administering the treatment, such that his/her experience, knowledge, and expertise can be utilized over a longer period of time within each day, and in the long term. In some embodiments, the 3D model of the patient's body can be presented in lieu of a full-color photographic images or video of the patient to the remote expert, such that the patient's discomfort and concern related to body image and privacy can be addressed and relieved.

In some embodiments, various sensors are provided at the local site to collect sensor information during treatment. The sensor information is processed in conjunction with the treatment being administered and the result of the analysis is provided to the local operator and/or remote expert in real-time such that suitable adjustment may be made. For example, the remote expert may be presented with the changes in the user's posture, regional temperatures of various parts of the patient's body, stiffness of various parts of the patient's body, heart rate, blood pressure, respiratory rate, perspiration, etc., and adjust the treatment procedures and/or treatment locations on the patient's body accordingly. The additional sensor feedback and analysis results help the remote expert to perform better guidance during treatment and adjust treatment in real-time in accordance with the patient's conditions and tolerance to the treatment.

In some embodiments, in addition to a local treatment operator, a therapeutic robot (e.g., robot arms, message pads on chair or bed, movable pressure applicators, etc.) located at the local site is utilized and controlled to administer at least some of the physical treatments applied to the patient's body. For example, acupuncture needle insertion and removal, heat application via infrared light or direct contact, ice pack application, pressure application via applicators of various shapes and sizes, application of rolling and massage motions in accordance with a movement path, controlled stretching of a part of the body, etc. can be performed by the therapeutic robot in accordance with the instructions received from the central computer, the patient, the local treatment operator, and/or the remote expert. The robot's motion is accurate and fully adjustable, and can continuously function for extended period of time without fatigue like a human operator or practitioner would be. The robot is easy to sanitize and also gives the patient more privacy.

In one aspect, a method of providing remotely-guided physical treatment is performed at a computing device having one or more processors and memory, wherein the computing device is communicably coupled to a therapeutic robot, and to a guidance device including a first display generation component and a first input device, and wherein the therapeutic robot is collocated with a treatment subject and the guidance device is collocated with a treatment guidance provider during a physical treatment session. The method includes: receiving one or more full-body images of the treatment subject; generating a plurality of key physical points for the treatment subject, including: determining a plurality of shape parameters and posture parameters of the treatment subject from the one or more full-body images of the treatment subject; identifying a first three-dimensional human body template that corresponds to the plurality of shape parameters and posture parameters of the treatment subject, wherein the first three-dimensional human body template has a corresponding set of key physical points; and fitting the identified first three-dimensional human body template to the one or more full-body images of the treatment subject, wherein the fitting causes adjustments to locations of at least one of the corresponding set of key physical points of the first three-dimensional human body template; and providing the adjusted locations of the corresponding set of key physical points of the first three-dimensional human body template to the guidance device, wherein the adjusted locations of the corresponding set of key physical points of the first three-dimensional human body template provides a basis for a treatment procedure that is specified by the treatment guidance provider during the physical treatment session.

In accordance with some implementations, a computing system includes one or more processors, memory, and one or more programs; the one or more programs are stored in the memory and configured to be executed by the one or more processors and the one or more programs include instructions for performing the operations of any of the methods described above. In accordance with some implementations, a non-transitory computer readable storage medium has stored therein instructions which when executed by a computing system with one or more processors, cause the computing system to perform the operations of any of the methods described above. In accordance with some implementations, a computing system includes means for performing the operations of any of the methods described above.

Additional advantages of the disclosed systems and methods are described throughout this disclosure, and/or are apparent to a person skilled in the art in light of the disclosure provided herein.

BRIEF DESCRIPTION OF THE DRAWINGS

For a better understanding of the various described implementations, reference should be made to the Description of Implementations below, in conjunction with the following drawings in which like reference numerals refer to corresponding parts throughout the figures.

FIG. 6 is a flowchart of a method of providing remotely-guided acupuncture and physical manipulations, in accordance with some embodiments.

Like reference numerals refer to corresponding parts throughout the several views of the drawings.

DESCRIPTION OF IMPLEMENTATIONS

Figure 1A:
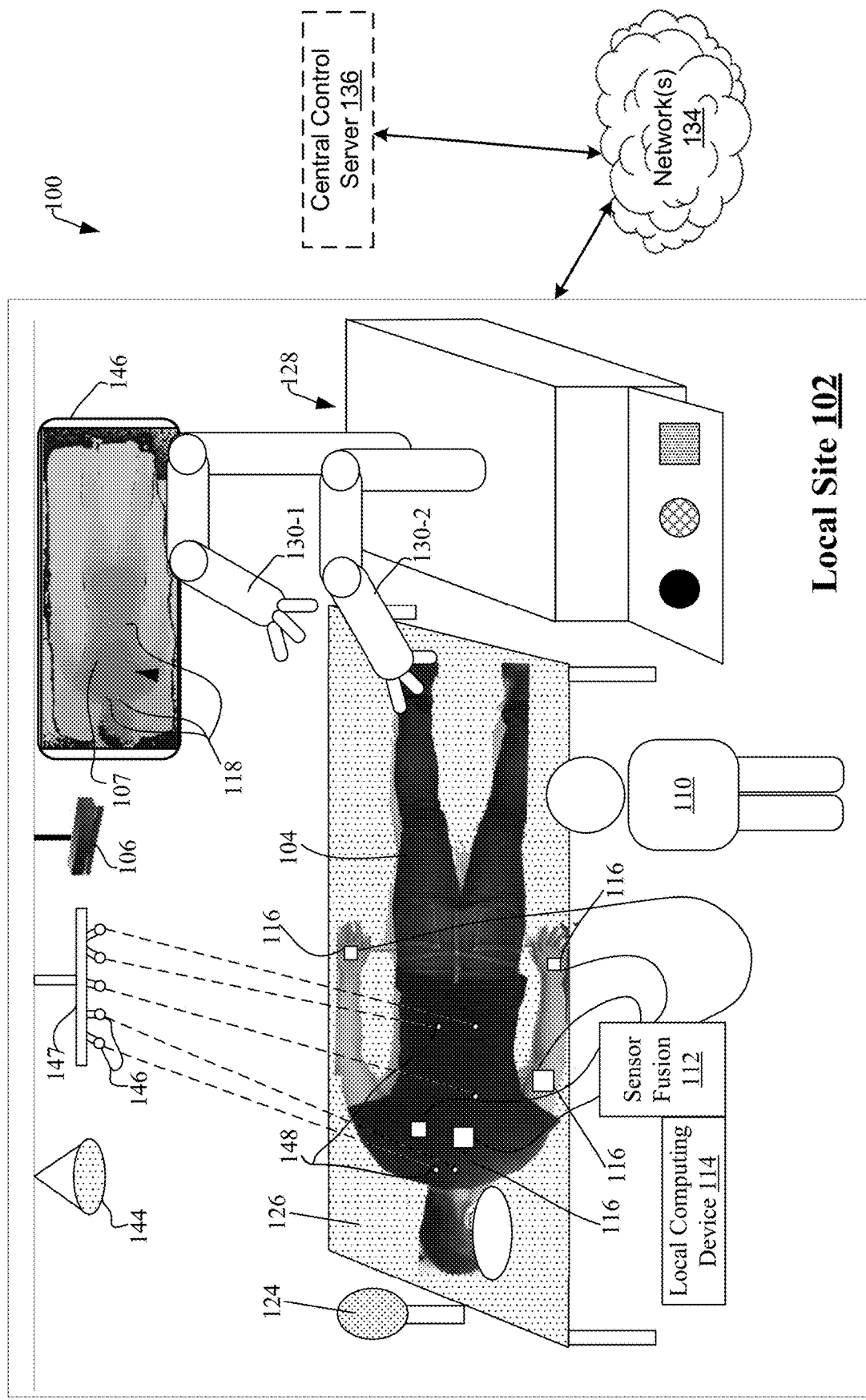
FIG. 1A is an exemplary local site of an exemplary treatment environment that provides remotely-guided acupuncture and therapeutic physical manipulations to a patient, in accordance with some embodiments.

This disclosure provides system and method for providing remotely-guided acupuncture and therapeutic physical manipulations in accordance with various embodiments.

Remotely-guided acupuncture and therapeutic physical manipulations have advantages over in-person treatment by skilled practitioners due to its flexibility and reduced demand on the skill-levels, physical presence, and/or physical strength and stamina of the treatment operators. A single skilled practitioner can provide remote assistance and guidance to a great number of local sites staffed with less skilled human treatment operators, remotely guided therapeutic robots, or just the patients themselves. This way, a greater number of patients can be treated, without the patients having to travel long distances or accommodating inconvenient treatment schedules. At the same time, the expertise of the remote expert can be utilized for complex diagnosis and treatment plan designs, with the aid of computer-generated key physical points that are fitted to the individual patients' particular body parameters. The accuracy of the diagnosis and treatment plan generation can be improved because of the combination of expert input and vast knowledge base of the control computer that generates the key physical points for the patient's body.

With the availability of remotely-guided treatment plans and real-time adjustment and guidance input from the remote expert, patients who are traditionally reluctant to go to such direct contact physical manipulation therapies can benefit from these types of treatments. For example, some patients do not want to undress in front of a real human practitioner or be directly touched by a human practitioner for various reasons (e.g., body image, modesty, religion, hygiene, etc.). The remote guidance system disclosed herein allows the patient to be alone in a treatment room or his/her own home, and have the treatment procedure performed by a robot or by himself/herself, with the guidance provided by a trained computer system and a skilled expert in real-time based on real-time images of his/her body and posture. The skilled expert does not need to see a color image of the patient or know the patient's identity, when providing the remote guidance input based on a three-D model of the patient's body (e.g., a mono-color depth image) and corresponding key physical points generated by the central computer. The skilled expert can explore the surface haptic characteristics of the three-D model and receive haptic feedback generated based on physics simulation via a haptic-enabled input device. The skilled expert also receives real-time sensor information collected from the patient's body and patient's verbal feedback during treatment. These further helps to reduce the limitations of a remote consultation, and improves the accuracy of the remote guidance provided by the skilled expert.

With the use of a therapeutic robot at the local site, the physical demand on the treatment staff is reduced. Instead of using fixed programs and instructions that are generic to many patients, the therapeutic robot can deliver customized treatment based on preprogrammed instructions with intermittent aid of a remotely located human expert. On the one hand, the robot is programmed to perform various low level or intermediate level tasks in accordance with environment input collected via on-board sensors and/or through a network, on the other hand, a human expert can intervene indirectly at suitable times in accordance with actual real-time visual and haptic rendering of the patient's body based on streaming RGBD data received from the sensors collocated with the patient and key physical points generated based on the streaming RGBD data (e.g., based on a three-dimensional model generated from the RGBD data). The generation of key physical points and tracking of the key physical points during the treatment is based on a model trained with expert annotated images of many patients with varied physical characteristics and therapeutic needs. As a result, the locations of the key physical points presented to the remote expert for treatment plan generation and used by the robot for performing the treatment procedures that are highly customized and accurate for the individual patients.

Individual features or combinations of features of the remotely-guided physical treatment system as described herein in various embodiments will further the advantages set forth above and/or provide additional advantages which will be elaborated on in more detail or will be apparent to a person skilled in the art in light the present disclosure.

Reference will now be made in detail to embodiments, examples of which are illustrated in the accompanying drawings. In the following detailed description, numerous specific details are set forth in order to provide a thorough understanding of the various described embodiments. However, it will be apparent to one of ordinary skills in the art that the various described embodiments may be practiced without these specific details. In other instances, well-known methods, procedures, components, circuits, and networks have not been described in detail so as not to unnecessarily obscure aspects of the embodiments.

It will also be understood that, although the terms first, second, etc. are, in some instances, used herein to describe various elements, these elements should not be limited by these terms. These terms are only used to distinguish one element from another. For example, a first user interface could be termed a second user interface, and, similarly, a second user interface could be termed a first user interface, without departing from the scope of the various described implementations. The first user interface and the second user interface are both user interfaces, but they are not the same user interface.

The terminology used in the description of the various described implementations herein is for the purpose of describing particular implementations only and is not intended to be limiting. As used in the description of the various described implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is, optionally, construed to mean "when" or "upon" or "in response to determining" or "in response to detecting" or "in accordance with a determination that," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]" or "in accordance with a determination that [a stated condition or event] is detected," depending on the context.

It is to be appreciated that "remotely guided" may refer to control over a wired or wireless network, such as the Internet, or an intranet within an organization or household network, the exact distance or location from which the inputs from the human user is provided is not specifically limited, and the scope of the present teachings is not so limited, unless explicitly specified otherwise.

It is also to be appreciated that while the terms user, expert, human operator, administrator, technician, person, and the like may be used to refer to the person or persons acting in the context of some particularly situations described herein, these references do not limit the scope of the present teachings with respect to the person or persons who are performing such actions.

FIG. 1A is an exemplary local site 102 of a remotely guided physical treatment environment 100 in accordance with some embodiments.

At the local site 102 of the environment 100, a patient 104 is collocated with a number of sensors, including imaging sensors (e.g., depth camera 106, infrared sensors), physiological sensors 116 (e.g., blood pressure monitor, heart rate monitor, oxygen level monitor, EMG (Electromyography) sensors, temperature sensors, perspiration sensors, etc.), patient feedback sensors (e.g., pressure sensors, microphones 124). The patient 104 is positioned on a support surface 126, such as the top of a massage table, a motorized bed, or a treatment chair. All the sensors are optionally connected to a network 134 and configured to transmit collected sensor data to a central control server 136 (e.g., a central computing system) in real-time and be controlled by the central server in real-time over the network 134. In some embodiments, the sensors are optionally controlled manually (e.g., adjusting the camera view and zoom level) by a local operator 110 via an input interface of the sensors.

In some embodiments, the imaging sensors 106 are configured to capture visual and depth data of the local site (e.g., Light Detection and Ranging (LIDAR), or RGBD cameras for capturing RGB colored image data and corresponding depth data of the scene). In some embodiments, the imaging sensors 106 (e.g., infrared cameras) are configured to capture a heat map of the patient's body to indicate the body's reaction to the treatment or indicate blood circulation state and sites of injury of the patient. In some embodiments, the imaging sensors 106 are located above the patient's body while the patient is lying or sitting on the support surface 126. In some embodiments, some imaging sensors are used to capture an initial set of images of the patient from multiple directions while the patient is in a standing posture to generate a full body three-dimensional model of the patient, before the patient lies down or sits down on the support surface 126. In some embodiments, the imaging sensors 106 are controlled by the central server 136 to adjust a camera angle and/or zoom level based on the treat location and treatment procedure currently being used.

In some embodiments, the physiological sensors 116 (e.g., blood pressure monitor, heart rate monitor, oxygen level monitor, EMG (Electromyography) sensors, temperature sensors, perspiration sensors, etc.) are used to collect baseline patient physiological data, and physiological response data during the treatment or particular sub-portions of the treatment procedures. The response data from different sensors are correlated by time through a sensor fusion process (e.g., in sensor fusion module 112 of the local computing device 114), and provided to an analysis model on the central control server 136 over the network 134. The analysis results, such as increased/reduced muscle/mental stress level, increased/decreased comfort level, increased/decreased mobility/flexibility level, increased/decreased pain, increased/decreased circulation, and other treatment advocacy levels etc., causes the analysis model to generate a recommendation regarding changes in the currently administered treatment procedure or plan.

At the local site 102 of the environment 100, a therapeutic robot 128 (e.g., a robot including robot arms 130-1 and 130-2 and control unit 132) is collocated with the patient 104. The robot 128 is connected to a network 134 and receives instructions from the central control server 136 over the network 134. In some embodiments, the central control server 136 is collocated with the robot 128 (e.g., in the same room). In some embodiments, the central control server 136 is within the same local area network as the robot (e.g., in the same treatment facility). In some embodiments, the central control server 136 is connected to the robot 128 over a wide area network (e.g., the Internet). In some embodiments, multiple robots located at multiple locations are connected and controlled by the same central control server 136 at the same time.

In some embodiments, the robot 128 has multiple attachments (e.g., acupuncture needle ejector, massage roller, acupressure probe, heat pad, ice pad, electrodes, clamps, grabber, etc.) that can be used (e.g., the robot can automatically select the selected attachments based on instructions from a human operator (e.g., local operator 110 or a remote expert 108 located at the remote site 105)) for different types of treatment procedures (e.g., acupuncture, massage, acupressure, heat, ice, electric muscle stimulation, pressure, stretching, etc.) and/or treatment locations (e.g., pressure points on the head, neck, shoulders, and other parts of the body, joints, muscles, skin, etc.) on the patient's body. In some embodiments, the sensors (e.g., sensors 106, 116, 124, etc.) are optionally controlled manually (e.g., adjusting the camera view and zoom level) by a local operator (e.g., operator 110) via an input interface of the sensors.

In some embodiments, at least some of the physiological sensors and patient feedback sensors are located on the robot 128 and moves with the robot (e.g., with the robot arms 130) to various locations of the patient's body during a treatment procedure. For example, one or more pressure sensors, perspiration sensors, temperature sensors are located on the robot finger tips used during massage and physical manipulations, to detect sites of cramped muscles, sites of inflammation or injury, sites of discomfort or pain, etc., and physiological changes (e.g., increased circulation, relaxation, stiffness, etc.) to the treated sites during various treatment procedures. In some embodiments, at least some of the physiological sensors and patient feedback sensors are attached to fixed locations on the patient's body. For example, a pressure sensor is placed in the patient's hand, and the patient can squeeze it if the treatment (e.g., acupressure, massage, stretching, heat, electric stimulation) is applied with too much force or strength. Other examples include blood pressure monitor, heart rate monitor, and EMG monitors that are attached to fixed locations on the patient's body and transmits sensor data to the local computing device 114 and sensor fusion module 112 in real-time.

In some embodiments, multiple parts (e.g., two robot hands or arms 130 with different primary roles and/or attachments) of the robot 128 can work in a coordinated manner in accordance with the high-level instructions provided by the central control server 136, the remote expert 108, and/or the local operator 110. For example, the robot 128 has onboard processing capabilities to perform low level functions such as moving, pulling, pushing, vibrating, grabbing, moving in a particular selected pattern, and stopping when there is more than a threshold amount of resistance, etc. In some embodiments, the robot 128 has onboard processing capabilities to perform intermediate level tasks, such as grabbing and stretching a limb in a preset direction, applying heat to a treatment site, injecting a needle, removing a needle, applying shiatsu massage to a treatment site, applying percussion massage to a treatment site, applying electric stimulation treatment to a treatment site, wipe a treatment site on the patient's body, applying ointment on a treatment site on the patient's body, helping the patient to lie down or sit up, helping the patient to turn to a required treatment posture, etc. The robot 128 is controlled by the central control server 136 which provides a treatment plan in terms of the low level or intermediate level tasks that can be performed by the robot, where the treatment plan is for accomplishing a high-level instruction provided by the remote expert or the treatment selection program of the central server 136.

In some embodiments, the user feedback sensors include a microphone 124 which captures the sounds of a user (e.g., the patient 104) during treatment. The user may verbally communicate pain or discomfort during treatment, answer the remote expert's questions, or ask questions to the remote expert 108, via the microphone 124. In some embodiments, the patient's speech input (e.g., answers, questions, and comments) during various portions of the treatment session (e.g., intake, diagnosis, treatment, and feedback portions) are analyzed and transcribed by the local computing device 114 automatically into text for record keeping and future improvement of the system.

In some embodiments, the local site 102 includes a number of output devices that provide feedback and information to the patient 104 and the local operator 110. In some embodiments, the local output devices include a display generation component 146, such as a display or a projector, that is used to display a three-dimensional model of the user's body as seen by the remote expert, and current treatment information, such as key physical points 118 identified on the patient's body, a current portion of the body that is being manipulated in treatment, and name and explanation of the treatment procedure. In some embodiments, the display also includes an image of the remote expert 108. In some embodiments, the patient's 3D model, the key physical points, and other treatment information are updated in real-time, as the patient shifts his body or change his posture, as the remote expert modifies the locations of the automatically identified key physical points or identifies a subset of the key physical points as targeted points for treatment, as the remote expert identifies or changes treatment procedures, and/or as a treatment procedure is performed or completed, etc.

In some embodiments, the output devices include a speaker 144 for outputting verbal questions, answers, and instructions from the remote expert 108 to the patient 104 and/or the local operator 110 during the treatment session.

In some embodiments, the local site 102 includes a projector 140 for projecting the identified key physical points (or a subset thereof that are relevant to the current treatment procedure) to their corresponding locations onto the patient's body. In some embodiments, the projector 140 is mounted overhead above the patient 104. In some embodiments, the projector 140 is attached to a movable robot arm and can be moved close to a portion of the patient's body that is the subject of the current treatment session (e.g., when the actual treatment is carried out by the patient himself or by the local operator, instead of the robot). In some embodiments, the projector includes multiple light sources 146 that are each individually controlled by the remote server 136 to project a respective light spot 148 onto a respective portion of the patient's body. The precise direction of each light source is calculated based on the coordinates of the spot in three-dimensional space in accordance with the position of the patient's body and the location of a respective key physical point on the patient's body. In some embodiments, the images captured with the light spots projected on the patient's body are provided back to the central control server 136 and used to adjust the three-dimensional model of the patient's body, until the actual locations of the light spots projected on the patient's body are aligned with the calculated locations of the light spots on the patient's body at that time.

In some embodiments, the robot arms 130 include sensors that detect and track the locations of the light spots 148 projected onto the patient's body during a treatment procedure, such that the treatment are applied to the correct positions on the patient's body at all times even when the patients moves or changes his/her postures slightly during the treatment. In some embodiments, the projector 140 has a sensor that detects the locations of the robot arms 130 and adjusts its own location and orientations such that the light from the light sources 146 is not blocked by the robot arms 130 on its way to the patient's body.

In some embodiments, at the local site 102, the support surface 126 includes various sensors for collecting physiological feedback and patient feedback. In some embodiments, the support surface 126 also includes various movable components for performing at least part of the treatment procedures. For example, the support surface 126 is the surface of a massage table, and includes balls or round-tipped cylinders that can be moved upward individually against the patient's body to apply various levels of pressure to selected points on the patient's body. The support surface 126 optionally includes massage rollers that travel on the support surface 126 to exert massages on the patient's body with a selected movement pattern. For example, the patient may lie on his back and have his lower back massaged by the rollers with circular motions and up and down motions, once the remote expert has specified or approved the automatically generated motion path for the massage that is tailored for the patient's body. Allowing the patient to lie on his back when receiving the massage is sometimes more comfortable and relaxing for the patient. Because the massage is executed by the massage table according to the 3D model of the patient's body, there is no need for the patient to lie facing down because there is no need for the therapist to see and manipulate the patient's back from above. The moving components of the massage table receives instructions from the central control server 136, and adjusts its movement path of the moving components in real-time when the 3D model generated from current images captured by the 3D camera indicates that the patients has shifted his/her body during the massage.

In some embodiments, a human treatment operator 110 (e.g., an assistant doctor, a nurse, a caregiver, a family member or a friend of the patient, etc.) is present at the local site 102. The treatment operator 110 can help to perform the treatment in accordance with information and the instructions (e.g., output via the speaker 144 or display generation component 146) provided by the remote expert or the central control server 136. In some embodiments, the treatment operator 110 helps to reposition the patient 104 or keep the patient 104 still during the initial imaging stage, or to help changing the attachments of the robot 128 for particular treatment procedures that are selected by the remote expert 108. In some embodiments, the human operator 110 can follow the demonstration of the remote expert 108 and perform the corresponding treatment procedure on the patient 104 based on the positions of the light spots 148 projected onto the patient's body.

Figure 1B:
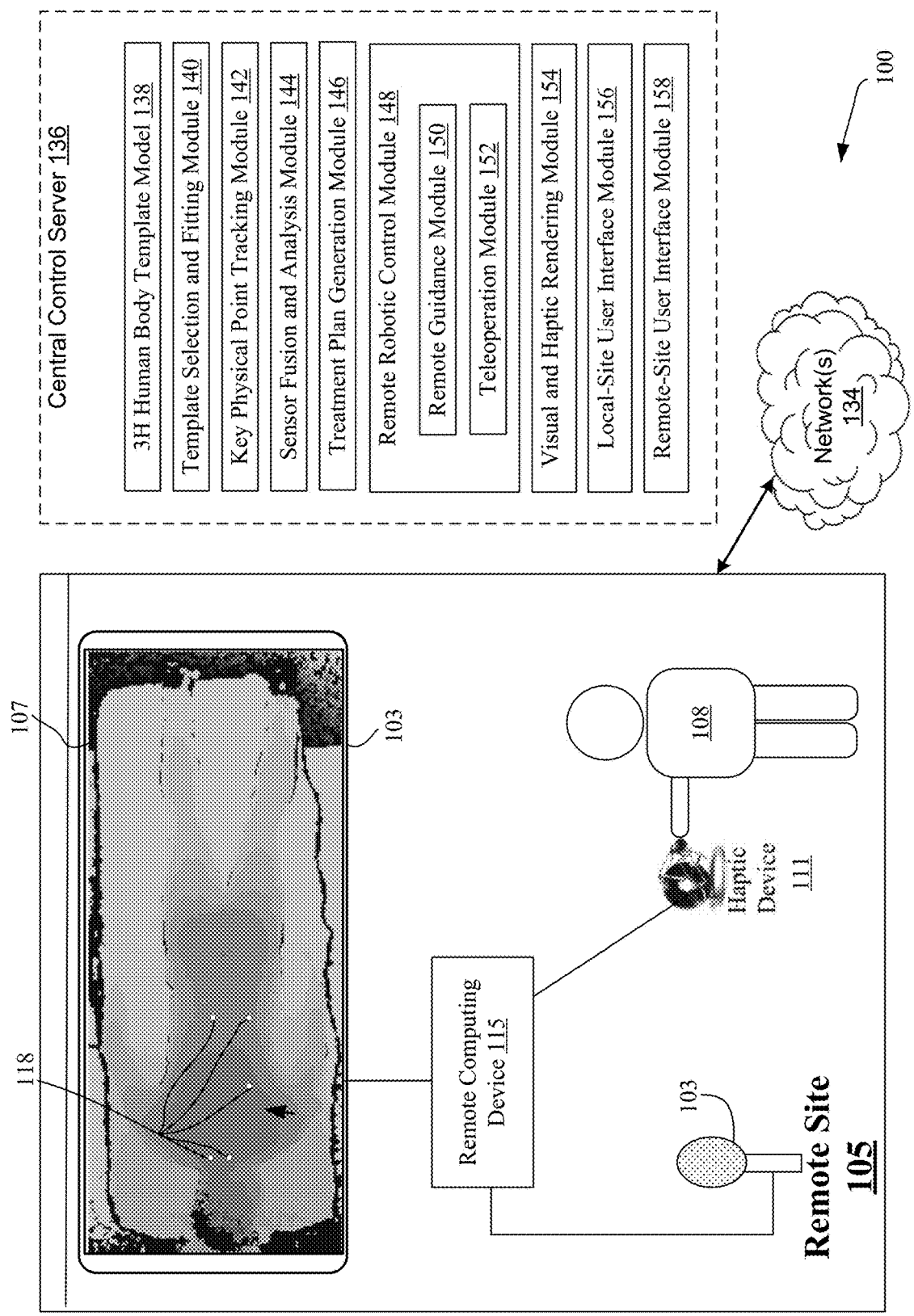
FIG. 1B is an exemplary remote site of the exemplary treatment environment that provides remotely-guided acupuncture and therapeutic physical manipulations to a patient, in accordance with some embodiments.

FIG. 1B is an exemplary remote site 105 of the exemplary treatment environment 100 that provides remotely-guided acupuncture and therapeutic physical manipulations to a patient (e.g., patient 104 in FIG. 1A), in accordance with some embodiment.

At the remote site 105 of the environment 100, a display generation component 103, such as a display, a projector, a heads up display or the like, is used to display images of the patient 104 captured by the imaging sensors 106 located at the local site 102. In some embodiments, in addition to full color images and infrared images, a virtualized version of the patient's body 107 captured by the depth camera 106 is displayed. The full color images and corresponding depth data that are streamed from the image sensors 106 (e.g., depth camera) are used to generate the virtualized version of the patient in the form of a point cloud or other three-dimensional representation of the patient, such that the virtualized version of the patient's body 107 that is visually presented at the remote site 105 via the display generation component 103 corresponds closely to the state of the patient 104 at the local site 102 at substantially the same time.

In some embodiments, the virtualized version of the patient 107 is received from the control server 136, where the control server 136 performs computations necessary to generate and continuously update the virtualized version of the patient based on the streaming image and depth data received from the depth camera 106. In some embodiments, the display generation component 103 also overlays automatically generated key physical points 118 received from the central control server 136 on the virtualized version of the patient 107 as shown on the display 103. In some embodiments, sensors data received from physiological sensors (e.g., sensors 116), user feedback sensors 124, and analysis results of the sensor data (e.g., received from the local site 102 or central server 136) are also displayed on display generation component 103 at the remote site 105.

In some embodiments, in addition to the display generation component 103, one or more input devices (e.g., a touch-sensitive surface, such as a touch-sensitive remote control, or a touch-screen display that also serves as the display generation component, a mouse, a joystick, a wand controller, a microphone 109 and/or cameras tracking the position of one or more features of the user (e.g., expert 108) such as the user's hands) is utilized by the remote expert 108 to provide inputs and instructions that will be utilized in guiding the treatment (e.g., controlling the robot 128 or directing the local operator 110). The one or more input devices include a haptic-enabled input device 111 (e.g., a three-dimensional haptic-enabled pointing device, a haptic-enabled glove, etc.) that generates force, motion, and/or texture feedback to the hand(s) of the remote expert 108 in accordance with simulated physical characteristics and physical interactions that occurs at a location on the virtualized version of the patient's body 107 that corresponds to the current movement and position inputs provided via the input device 111. For example, when the movement and position inputs provided via the input device 111 corresponds to movement along a simulated surface on the virtualized version of the patient's body 107 corresponding to the patient's shoulder, the haptic feedback generated on the haptic-enabled input device 111 will elicit haptic sensations in the user's hands that correspond to the shape, size, friction, texture, and hardness of the patient's shoulder. The real-time haptic feedback in conjunction with the visual rendering of the virtualized version of the patient's body allows the remote expert 108 to accurately experience and assess the problem site on the patient's body, and to provide more accurate and prudent guidance on the patient's treatment procedures.

In some embodiments, the input devices at the remote site 105 optionally supports teleoperation as well, and the expert 108 can temporarily take over control of the robot arms 130 (using precise direct movement control that will be replicated by the robot, as opposed to command type control that is interpreted by the robot and executed based on pre-established task execution instructions) and perform the treatment at the desired locations on the patient's body based on images received from the local site. At other times, the remote expert allows the robot to operate fully autonomously according to pre-established task execution instructions after the remote expert has provided the remote guidance required to start the treatment procedures.

In some embodiments, the human operator 108 uses the haptic-enabled input device 111 to interact with virtualized surfaces on the virtualized version of the patient's body 107, and mark the virtualized version of the patient's body with additional key physical points or adjust the locations of the automatically generated key physical points. In some embodiments, when new key physical points are specified by the remote expert, and/or when locations of the automatically generated key physical points are adjusted by the remote experts, the locations of the new key physical points and the adjusted locations of the key physical points are transmitted to the central control server 136, and the central control server 136 correspondingly update the display and projector instructions sent to the remote and local sites.

In some embodiments, the remote expert can use the haptic-enabled input device to mark a path for massages on the virtualized version of the patient's body. The path is provided to the central control server and relayed to the robot or displayed on the display located at the local site 102, which is then implemented during the treatment procedure.

In addition to the equipment collocated with the patient 104 (e.g., patient-side computing device 114) and the equipment (e.g., expert-side computing device 115) collocated with the remote expert 108, the remotely guided physical treatment environment 100 includes a central computing device (e.g., the central control server 136) that handles the extensive computation tasks related to visual and haptic data processing and rendering, generating the virtualized three dimensional model for the patient and generating the key physical points for the virtualized three dimensional model, updating the three dimensional model and tracking the key physical points in accordance with movement of the patient in the streamed depth images, and updating the key physical points based on expert input or feedback from the local site (e.g., sensors on the projectors), and generating treatment procedures and treatment plans with intermediate level instructions and workflows that bridge the gap between the high-level instructions from the remote expert and the low-level instructions executable by the robot. The central control server 136 is connected to the local site equipment 114 and/or the remote site equipment 115 via one or more networks 134. In some embodiments, the central control server 136 is collocated with the robot 128. In some embodiments, the central control server 136 is collocated with the remote expert 108. In some embodiments, the central control server 136 is not collocated with either the robot 128 or the remote expert 108.

In some embodiments, the central control server 136 handles the computation related to real-time, simultaneous localization and mapping (SLAM) using real-time dense surface mapping and tracking techniques, such as Kinect-Fusion. In some embodiments, other real-time three-dimensional modeling methods are used to generate a virtualized three-dimensional or pseudo-three-dimensional representation of the patient based on the streaming image and depth data collected from the local site 102. The central computing device generates a point cloud during every time step of the streaming RGBD data using KinectFusion for visual rendering. The central computing device also performs haptic render and physics simulation for interactions between the remote expert and the virtualized version of the patient's body, e.g., via a virtual pointer. In some embodiments, the virtualized version of the patient's body is represented by a three-dimensional point cloud. In some embodiments, the virtualized version of the patient's body is represented by a three-dimensional mesh that includes simulated surfaces that correspond to physical surfaces of the patient's body.

In some embodiments, the central control server 136 implements an image processing model that has been trained on annotated depth images of patient's, where the annotations include locations of key physical points on the patient's bodies of different shapes, sizes, and other visual characteristics. When the model training is completed, the model is used to process depth images of the current patient, and deriving a three-dimensional model of the patient's body, as well as parameters that are used to determine the locations of the key physical points on the patient's body. In some embodiments, a template-based model is used, and the best fitting template for the patient is selected based on the shape parameters of the patient's body. Once the key physical points are generated for the patient's body, the locations of the key physical points are continuously tracked as the patient's body moves or changes posture. More details of the generation and tracking of the key physical points are described with respect to FIG. 3.

Figure 5:
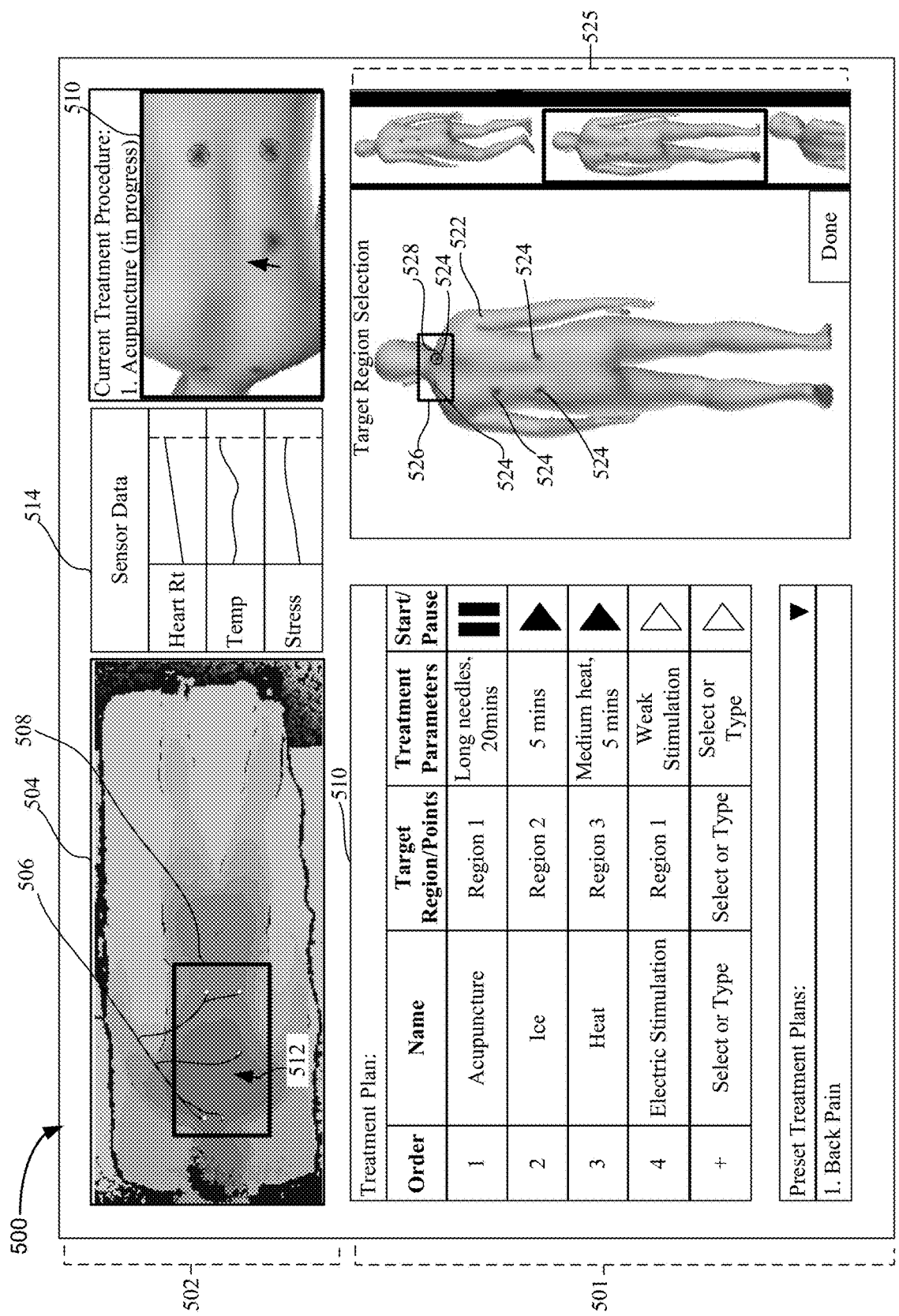
FIG. 5 illustrates an exemplary user interface for providing remote guidance for treatment of a patient by a remote expert, in accordance with some embodiments.

In some embodiments, the central control server 136 includes a treatment planner that generates a set of treatment procedures and treatment actions for each treatment procedure based on the key physical points and the input from the expert 108 (e.g., input provided via the user interface 500 shown in FIG. 5). The treatment planner takes into account both the characteristics of the patient's body, symptoms, locations of the key physical points, the input of the remote expert, and the feedback detected during the treatment procedures and/or earlier treatment procedures, and generates and modifies the treat plan in accordance with preprogrammed treatment planning instructions.

In some embodiments, the central control server 136 includes one or more of the following modules to implement its functions: a 3D Human Body Template Model 138, a Template Selection and Fitting Module 140, a Key Physical Points Tracking Module 142, a Sensor Fusion and Analysis Module 144, a Treatment Plan Generation Module 146, a Remote Robotic Control Module 148 which further includes a Remote Guidance Module 150 and a Teleoperation Module 152, a Visual and Haptic Rendering Module 154, a Local Site User Interface Module 156, and a Remote Site User Interface Module 158.

Figure 2:
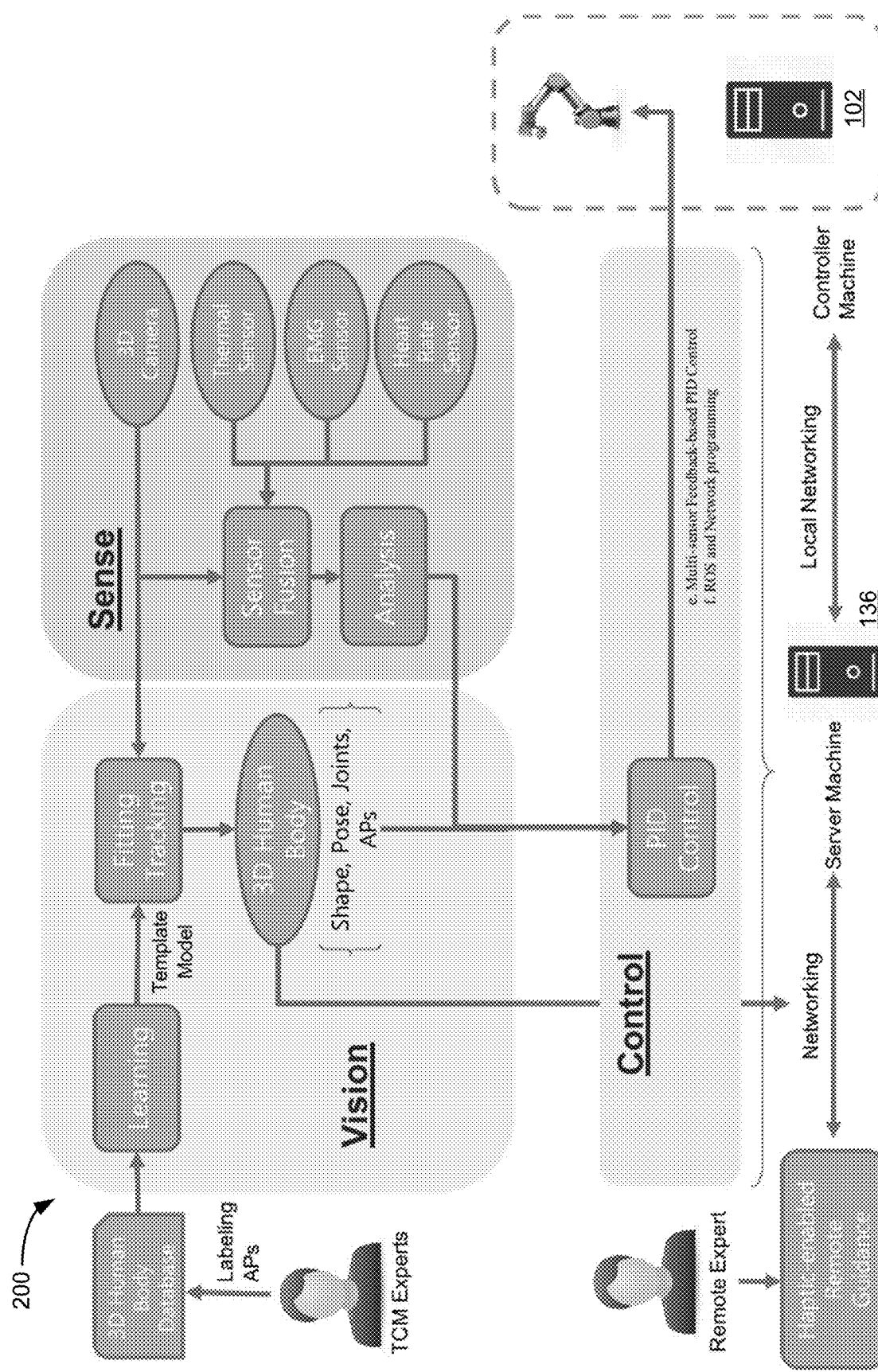
FIG. 2 is a block diagram illustrating an exemplary architecture that includes the remotely-guided treatment environment in accordance with some embodiments.

FIG. 2 is a block diagram illustrating an exemplary architecture 200 that includes the remotely-guided treatment environment 100 in accordance with some embodiments.

As described herein, a key component of the treatment environment is automatic generation of key physical points based on the patient's RGBD images and continued tracking of the key physical points during treatment when the patient moves or changes his/her postures.

In some embodiments, in order to establish a model for generating customized key physical points for the current patient, a three-dimensional human body database is first established. Images including color images and depth images of patients of various sizes, shapes, fitness levels, genders, ages, ethnicities, etc. are annotated by experts in physical treatment (e.g., traditional Chinese medicine experts, or physical therapists, experienced chiropractors, acupuncturist, massage therapists, etc.) to indicate locations for various types of key physical points (e.g., acupuncture points, muscles, joints, trigger points, etc.) relevant to various types of treatment procedures (e.g., acupuncture, electric stimulation, compression, acupressure, etc.) on the images. In some embodiments, the images of the patients are converted to three-dimensional models of the patients and the annotations are provided on the three-dimensional models. In some embodiments, the images are also labeled with various parameters that characterizes the visual characteristics of the patient's body in the images. The parameters include shape (e.g., actual shape or predefined categories of shapes) and sizes (e.g., general size, or actual dimensions) of various key parts of the human body (e.g., head, face, ears, neck, shoulder, lower back, abdomen, back, buttocks, left thigh, right thigh, left knee, right knee, left calf, right calf, left hand, right, hand, left wrist, right wrist, left foot, right foot, left sole, right sole, etc.). Other shape parameters optionally include muscle definition, fat content, swollenness, bruising, etc. In some embodiments, the images are also labeled with one or more pose parameters for the patients in the images. For example, the pose parameters include overall pose of the patient, such as sitting, lying facing down, lying facing up, lying sideways facing left, lying sideways facing right. Other pose parameters may be related to particular portions of the body, such as left leg bend to 45 degrees, arms on the side of torso, left arm raised up, head turn to the left side, eyes closed, etc. Annotations that are particular to certain parts of the body that are relevant to treatment as well as posture of the patient's body includes location and identities of joints, such as joints on the knees, hips, ankles, toes, writs, fingers, shoulders, spine, etc. Acupuncture points related to different health aspects, such as sleep, digestion, energy level, heart, liver, etc. are also annotated on the images. In some embodiments, the acupuncture points are optionally further annotated with the body functions that are related to the acupuncture points.

As described herein, reconstruction of a representation of the three-dimensional physical space in which the robot is operating needs to be performed in real-time with fair degree of accuracy in order for the user to provide appropriate and timely intervention. In order to facilitate real-time three-dimensional exploration, segmentation, marking, and interactions with the environment, haptic-rendering and physics simulation need to be performed in real-time in conjunction with the visualization of the environment. Since the visual and depth data that needs to be transmitted and processed is voluminous in nature, network latency needs to be managed in order to provide smooth, real-time operation and control based on such data communicated over networks with various latencies.

Once a training database is established with annotated images of the patients. The images and annotation data are used in training an image processing model. In some embodiments, a deep learning model is used to link images with corresponding parameters. In some embodiments, a template model is used to link the visual parameters of the patient's images (e.g., shape parameters and pose parameters) with locations of key physical points (e.g., muscles, joints, pressure points, acupuncture points, etc.).

When images of a new patient are received from the 3D cameras collocated with the new patient, the images are provided as input to the trained image processing model (e.g., a neural network model or a template model), and key physical points are generated for the input images based on the trained image processing model. In some embodiments, if the image processing model is a template-based model, the shape and posture parameters of the patient in the newly received images are used identify a closest matching template, and the locations of the key physical points in the closest matching template are used as the locations of the key physical points for the current patient. In some embodiments, the closest matching template is fitted to the images of the current patient, and the locations of the key physical points on the closest matching template are adjusted as a result of the stretching (during fitting), and the adjusted locations of the key physical points are used as the locations for the key physical points of the patient. In some embodiments, once a closest matching template is selected for a patient based on the visual parameters (e.g., shape and posture parameters), as small movements of the patient's body is identified in the streaming images (e.g., movement does not qualify as a new pose), the template is fitted to the new images and the locations of the key physical points are continuously updated based on the newly fitted template. In some embodiments, when a new pose is detected in the new images, a new template is identified based on the closest matching criteria. In some embodiments, when a new pose is required for a subsequent treatment procedure, the new template or two or more candidate templates can be preselected based on the shape parameters and the new pose parameters corresponding to the required next pose, to save processing time.

As shown in FIG. 2, sensor data from various sensors (e.g., image sensors (e.g., 3D images, infrared images, etc.), thermal sensors (e.g., temperature sensors, infrared sensors on the robot arms, etc.), physiological sensors (e.g., EMG sensors, heart rate sensors, etc.), patient feedback sensors (e.g., pressure sensors, microphone), etc.) are merged based on time (e.g., correlated based on the same or similar timestamps of the sensor data) and grouped based on indicator type (e.g., related to pain, stress, comfort, etc.) through a sensor fusion process, and the fused sensor data is analyzed and provided to the central control server 136 to be output as visual indications for various types of measures for determining whether the treatment is effective, comfortable, and/or painful to the patient, and how the treatment parameters may be adjusted to improve the effectiveness, comfort level, and tolerance level of the patient.

As shown in FIG. 2, the generated key physical points are provided to the central control server 136 and passed to the remote site (and optionally to the local site) for display. In some embodiments, instead of displaying full color images of the patient and overlaying the generated key physical points on the full color images. The central control server 136 generates a three-dimensional model of the patient's body. In some embodiments, the three-dimensional model is a template model that is fitted to the streamed images of the patient. In some embodiments, the three-dimensional model is a point cloud generated from the streaming images from the 3D camera. In some embodiments, in order to provide haptic interactions between the three-dimensional model of the patient and the remote expert, the central control server uses a Truncated Signed Distance Function (TSDF)-based haptic rendering method with streaming surfaces to ensure the smooth and robust haptic interaction with virtualized patient body.

In some embodiments, Fusion-based methods (e.g., KinectFusion) are used to perform localization and mapping of streaming visual and depth data. According to KinectFusion, the streaming RGBD data from the three-dimensional camera are fused and saves as a Truncated Signed Distance Function (TSDF). KinectFusion can provide the full-scene dense geometry to enable mixed reality. The present disclosure describes visual and haptic rendering with streaming surfaces generated by KinectFusion using an improved haptic rendering pipeline including collision detection, proxy update and force computation. This improved method is computationally efficient and integrate well with the KinectFusion framework.

As shown in the FIG. 2, the remote expert interacts with the three-dimensional model of the patient and optionally adjusts the locations of the key physical points through a user interface displaying the three-dimensional model and the key physical points. In some embodiments, the interaction is provided with a haptic enabled device such that the remote expert can experience the surface of the three-dimensional model with real size, shape, and texture feedback. In some embodiments, the remote expert selects a subset of the key physical points as target points for a selected treatment procedure. In some embodiments, the remote expert demonstrates the treatment procedure on the virtual three-dimensional model, such that the same procedure can be performed by the local operator, the patient, or the robot at the local site. In some embodiments, the remote expert specifies a sequence of treatment procedures, and also interact with the patient, and/or the local operator to inquire about the patient's symptoms, asking the patient or operator to adjust the patient's posture, and explain the treatment procedure and their purposes to the patient.

In some embodiments, the treatment plan including the treatment procedures and the locations of the key physical points targeted by the treatment procedures are sent to the robot located at the local site. The robot implements the treatment plan and performs the treatment procedures according to the locations of the key physical points and the instructions in the treatment plan. In some embodiments, the robot returns local feedback sensor data to the central control server, and the central control server continues to update the three-dimensional model of the patient's body, the locations of the key physical points, and the sensor data received from the local site, and send the updated data to the remote site, for the remote expert to update the treatment plan or treatment parameters for the treatment procedures included in the treatment plan accordingly.

FIG. 2 is merely an illustration of an exemplary architecture of a treatment environment. Other structure of the architecture is possible, and the architecture may include other components and communication routes, as will be apparent to the skilled person based on the present disclosure.

Figure 3:
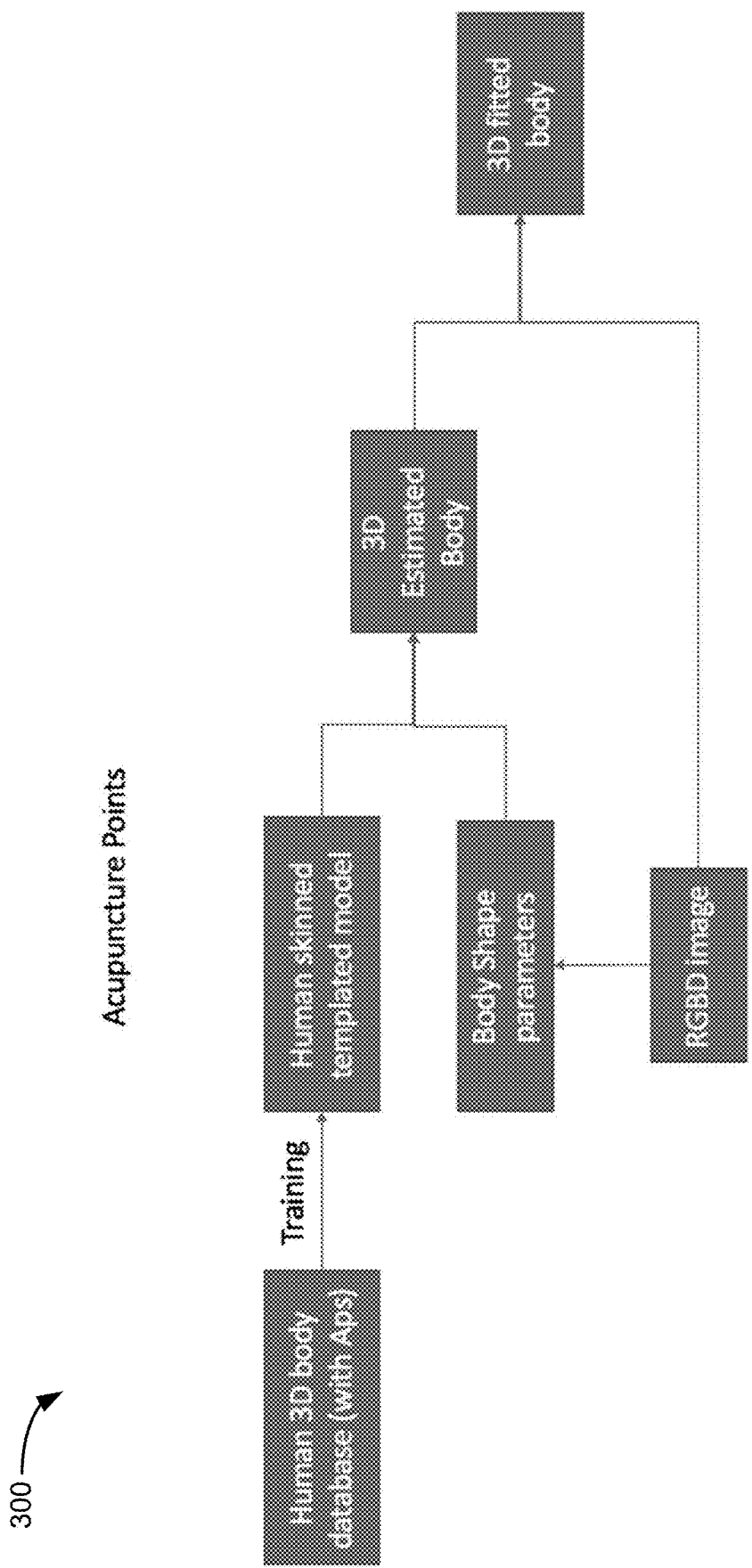
FIG. 3 illustrates an exemplary processing pipeline for training and using a template model for generating key physical points for a patient's body, in accordance with some embodiments

FIG. 3 illustrates an exemplary processing pipeline 300 for training and using a template model for generating key physical points for a patient's body, in accordance with some embodiments. As shown in FIG. 3, a database of three-dimensional models of human patient's bodies are annotated with various types of parameters, including shape parameters, posture parameters, joints parameters, and locations of key physical points on the three-dimensional model. The three-dimensional models are used in training to obtain a template model (e.g., human skinned template model). The template model includes a plurality of templates that have respective shape parameters, posture parameters, joint parameters, and key physical points that are representative of the human bodies represented in the training data. When one or more RGBD images of a patient are received from a local site, the images are processed to determine the body shape parameters and optionally posture parameters. In some embodiments, the posture parameters are manually entered by the patient or local operator. In some embodiments, the posture parameters are specified by the remote expert or the local operator, and the patient is positioned according to the specified posture parameters before the images of the patient are streamed. The template model uses the patient's body shape parameters as input to identify a best-matching template, e.g., with the minimized overall difference between an evaluation function based on the shape parameters of the templates and the shape parameters of the patient in the streamed images. Once the best-matched template is identified based on the shape and posture parameters, the best-matched template is used as an estimated three-dimensional model for the patient's body. The best-matched template is fitted to the actual shape parameters of the patient's body images, and various portions of the template are stretched, or shrunken. The fitting is performed with a minimized alteration to the best-matched template, and after the fitting, the locations of the key physical points on the fitted template are used as the locations of the automatically-generated key physical points for the patient in the current posture.

In some embodiments, during the treatment session, the patient may move slightly, and the movement of the patient causes the images streamed to the control server to change slightly, resulting in changes in the shape parameters of the patient's body. If the changes in the shape parameters are relatively small, e.g., smaller than preset threshold percentage, the previously selected template is not changed, and the template is fitted again to the patient's body in the new images, and the locations of the key physical points are updated accordingly as a result of the fitting. If the changes in the shape parameters are relatively large, e.g., larger than the preset threshold percentage, a new template is selected from the set of templates in the template model based on the new shape parameters derived from the new images. Once a new template is selected (e.g., a different template or the same template as before), the new template is fitted to the patient's body in the new images, and the locations of the key physical points are updated again based on the new locations of the key physical points on the fitted template. In some embodiments, if the posture of the patient changed (e.g., the patient lifted his leg or turned sideways), a new template is selected based on the shape parameters of the patient's body in the new images and the posture parameters of the patient's body in the new images. The new template is fitted to the patient's body in the new posture, and the locations of the key physical points on the fitted template are used as the locations of the automatically generated key physical points for the patient.

In some embodiments, when the locations of the key physical points generated for the patient are sent to the projector at the local site, and the projector projects light spots onto the patient's body based on the locations of the key physical points and the currently known shape and location of the patient's body, if the locations of the light spots do not align with the predicted locations of the key physical points on the patient's body, the differences are reported back to the central control server, and the central control server adjusts the three-dimensional model of the patient's body, and optionally reselects the template or readjusts the fitting between the template and the patient's body in the current images until the light spots and the predicted locations of the key physical points are sufficiently aligned at the local site.

Figure 4A:
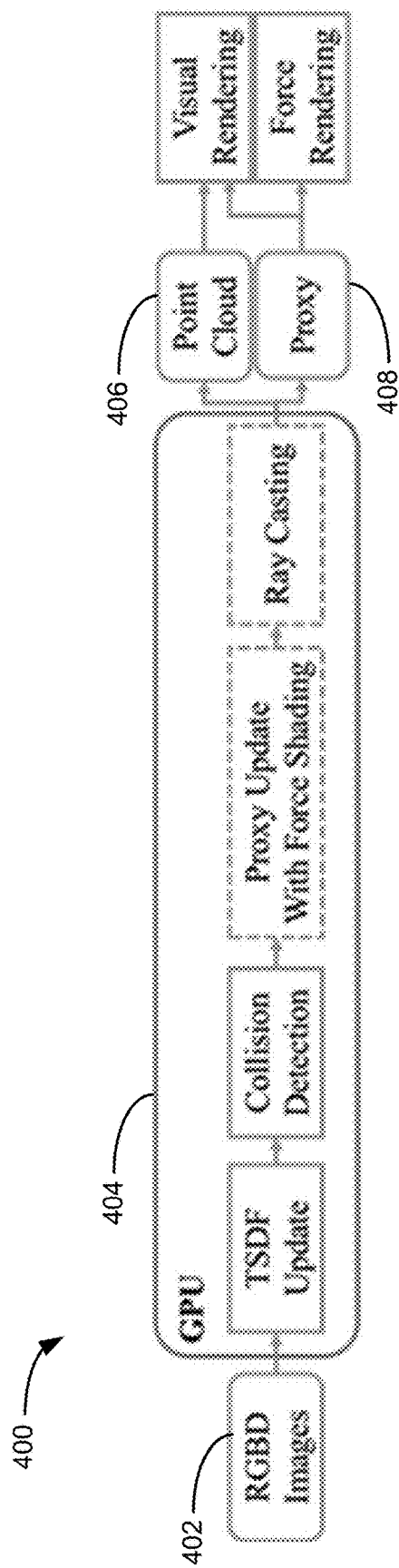
FIGS. 4A-4C illustrate an exemplary processing pipeline for real-time visual and haptic rendering at the remote site of the remotely-guided treatment environment, in accordance with some implementations.
Figure 4B:
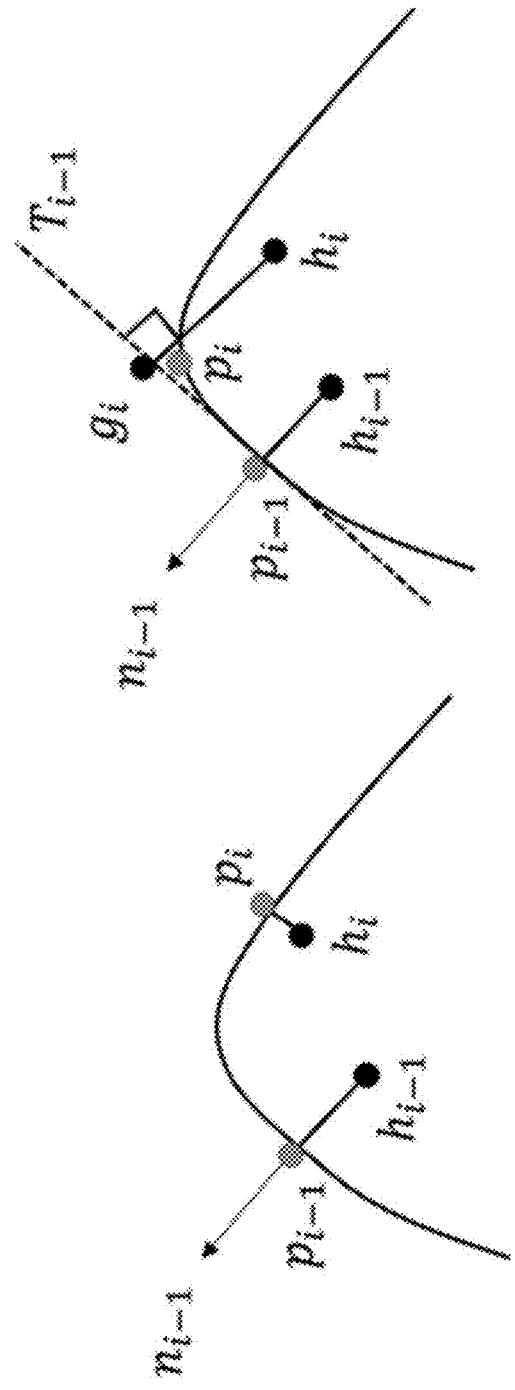
Figure 4C:
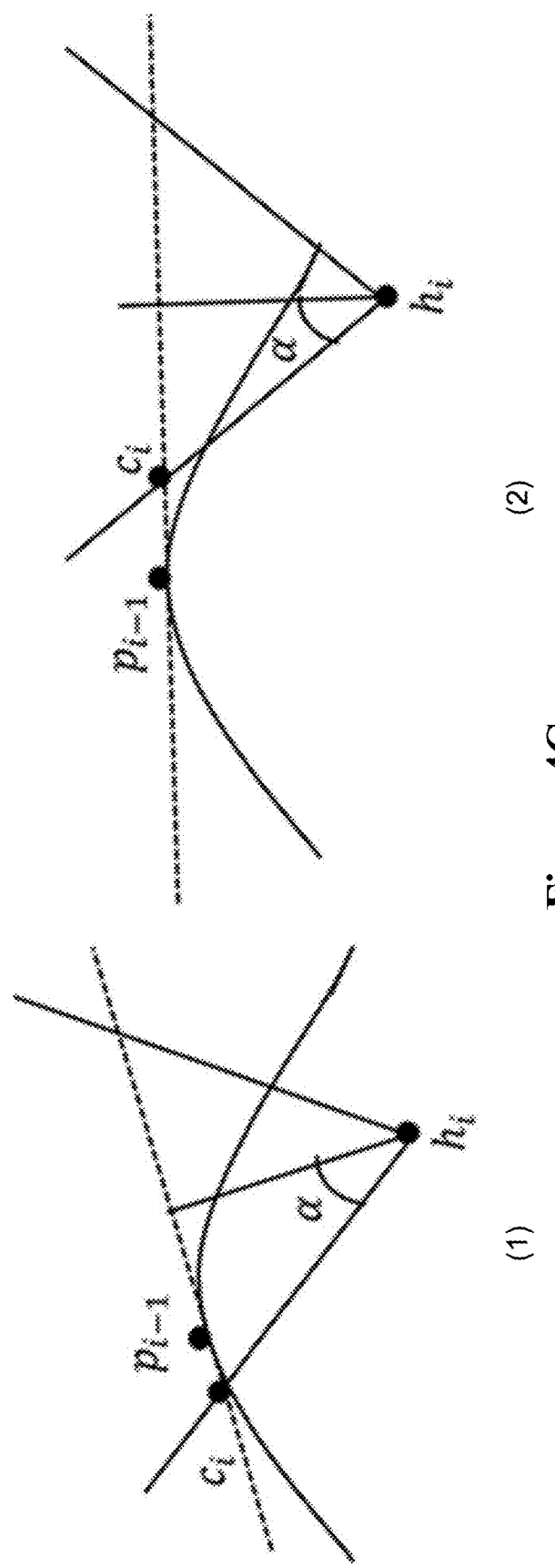

FIGS. 4A-4C illustrate an exemplary processing pipeline for real-time visual and haptic rendering at the remote site of the remotely-guided treatment environment, in accordance with some implementations.

As shown in FIG. 4A, RGBD data 402 received from the imaging sensors (e.g., 3D camera) collocated with the patient and the robot is streamed over a network and provided to a graphical processing unit 404 (GPU) on a central control server 136. Since KinectFusion is applied for dense mapping and localization, dense geometry is generated as the streaming surfaces of the 3D virtualized version of the patient's body. In the GPU 404, TSDF update is performed, followed by collision detection, and followed by proxy update with force shading and ray casting. The resulting data includes a point cloud 406 and proxy values 408 for all haptic interaction points (HIPs). The point cloud 406 and the proxy values 408 are utilized in visual rendering on a display (e.g., displays at the local site and the display at the remote site), and the proxy values 408 are utilized in force rendering on the haptic-enabled input device (e.g., input device 111).

In the present disclosure, a novel proxy update method with force shading is proposed, which is more efficient and guarantees the stable rendering at intersecting boundaries of different planes. Furthermore, the method allows addition of surface properties such as friction and haptic textures in haptic rendering.

Proxy update is a key-part of constraint-based haptic rendering, since the proxy is not only used to compute the force at an interaction point, but also rendered visually to the viewers. If the proxy update is not stable and smooth, the force rendering and visual rendering will not be smooth. Previously, a proxy update method that has been published uses gradient-based method to find the nearest surface point. As shown in FIG. 4B, FIG. 4B(1) on the left shows a scenario that the haptic interaction occurs on a surface with a sharp change in direction (e.g., interaction goes around a corner of a curved surface or the boundary of two intersecting planes). In this scenario, the haptic interaction point (HIP) is moved by the user from $h_{i-1}$ to $h_i$, and the proxy position is changed from $p_{i-1}$ to $p_i$, in accordance with previously disclosed haptic rendering methods. Since the proxy is always the nearest surface point according to the HIP in the previously disclosed method, the proxy undergoes a sudden change in position. In terms of user experience, it would feel as though the user's finger has suddenly "jumps" to the other side of the surface, and computed force is changed drastically to an almost reversed direction. This feels distracting, unrealistic, and confusing to the user.

Force shading is an algorithm for smooth haptic rendering. In this disclosure, a novel TSDF-based proxy update method with force shading is proposed. Different from previous force shading methods, the presently disclosed method focus on the TSDF data structure, which can be used in all of the fusion-based 3D reconstructions. Two scenarios are handled in the improved proxy updating method:

In some embodiments, the improved method described herein simulate surface properties to generate simulated friction forces, and different haptic sensations of textured surfaces. In some embodiments, the friction force can be simulated by a simple change using a known friction cone. The angle α defines a cone starting from the current HIP $h_i$, as shown in FIG. 5. The friction cone forms an interaction circle with the tangent plane from the previous proxy point $p_{i-1}$. In some embodiments, $\alpha = \arctan(\mu)$, where μ is a user defined friction coefficient. If the previous time step proxy $p_{i-1}$ is inside the interaction circle (e.g., as shown in FIG. 4C(1)), then the new proxy will be directly set to the same value as before: $p_i = p_{i-1}$. If the previous time step proxy $p_{i-1}$ is outside of the interaction circle (e.g., as shown in FIG. 4C(2)), then the goal position (approximated proxy) $g_i = c_i$, where $c_i$ is the point closest to $p_{i-1}$ on the interaction circle. These two scenarios correspond to simulated static friction and simulated dynamic friction. In some embodiments, the haptic texture is implemented by using a bump texture method which can generate the constraint for each point on the surface to change the normal.

FIG. 5 illustrates an exemplary user interface 500 for providing remote guidance for treatment of a patient by a remote expert, in accordance with some embodiments.

As shown in FIG. 5, the user interface 500 includes a real-time data display portion 502 and a treatment planning and adjustment region 501. In the real-time data display portion 502, a virtualized version of the patient's body 504 is displayed in a first region. The virtualized version of the patient's body 504 is operationally a point cloud generated from the streaming 3D images received from the local site 102. In some embodiments, the virtualized version of the patient's body 504 is a smooth mesh surface representing the depth and shape of the patient's body on the support surface at the local site. In some embodiments, the key physical points 506 that are automatically identified for the patient's body are overlaid on the virtualized version of the patient's body 504. In some embodiments, a target region selection window 508 is displayed overlaid on the virtualized version of the patient's body 504. The remote expert can slide the target region selection window 508 across different portions of the virtualized version of the patient's body and view them in the zoomed viewing region 510. By default, the window 508 is placed over a region of the virtualized version of the patient's body that is currently the target region of the currently executed treatment procedure. For example, during the treatment procedure, the remote expert can move the window 508 by dragging it using a virtual pointer 512, and the region of the patient's body within the window 508 will be displayed in zoomed viewing region 510. Once the remote expert releases the window 508, the window automatically goes back to the target region of the current treatment procedure, and the portion of the patient's body shown in zoomed viewing region 510 becomes the target region of the current treatment procedure. This user interface feature allows the remote expert to check on other portions of the patient's body during a treatment procedure, as if he or she is at the location of the patient. In some embodiments, the remote expert may temporarily lock the location of the window 508 after dragging it away from the default location by pressing a special key on the input device. In the zoomed viewing region 510, by default the status and progress of the current treatment procedure is shown. For example, as shown in FIG. 5, the currently executed treatment procedure is acupuncture on region 1 of the patient's body, with long needles, for 20 minutes. The zoomed viewing region 510 shows that two needles have been inserted into the five key physical points selected for the treatment procedure in region 1. As a new needle is inserted into the next key physical point, the key physical point will be highlighted as well (e.g., with a cross "x"). In some embodiments, the remote expert can explore the portion of the patient's body shown in the zoomed viewing region 510 using a haptic enabled input device. As virtual pointer 512 is dragged across the surface of the portion of the virtualized version of the patient's body shown in the zoomed viewing region 510, the central control computer provides haptic feedback to the expert's hand via the haptic enabled input device (e.g., device 111), such that the remote expert can experience the change in contour, texture, and stiffness of the patient's skin. The helps the remote expert better adjust the treatment procedure and the locations of the key physical points during the treatment procedure.

As shown in FIG. 5, sensor data from the local site is displayed in the sensor feedback display region 514. For example, patient's heart rate, temperature, stress level, etc. are shown in this region and are continuously updated during the treatment procedures. Some of these sensor data are raw sensor data, and some are aggregated sensor data. In some embodiments, some of the data is analysis results derived based on a combination of multiple types of sensor data. For example, stress level is a type of data that is derived from physiological responses (e.g., blood pressure, heart rate, perspiration, muscle tension, etc.) as well as other active user feedback data (e.g., pressure sensor on the user's hand, user's verbal communication, user's facial expression, etc.). The remote expert optionally selects the types of sensor data that he/she wants to display in this region, to determine the suitable treatment procedures. For example, if the purpose of the treatment is relaxation, the remote expert will place relevant sensor data for determining stress levels in display region 514. If the purpose of the treatment is pain reduction, the remote expert will place relevant sensor data for determining pain and discomfort in display region 514. In some embodiments, the user interface allows the remote expert to select a purpose for the treatment, and automatically populates the sensor data types into the sensor feedback display region 514.

In the user interface 500, treatment plan input region 516 is not dynamically updated in real-time. In the treatment plan specification region 516, the remote expert has selected multiple treatment procedures that are to be carried out in a current treatment session. In some embodiments, the treatment plan can be started, even before all of the treatment procedures have been specified. Sometimes, the later treatment procedures are determined by the remote expert based on the result of the earlier performed treatment procedures. For example, in the current treatment plan, the first treatment procedure is specified to be "acupuncture", and the user interface allows the remote expert to select a target region on the patient's body for each treatment procedure. After the target region for the treatment procedure is specified, the user interface allows the remote expert to select one or more treatment parameters for the treatment procedure. Once all the treatment parameters are specified, a control is displayed for the remote expert to send a command to start the treatment procedure. As shown in FIG. 5, the user interface 500 shows that the remote expert has specified three treatment procedures completely. The first treatment procedure is acupuncture, and it is to be applied to region 1 of the patient's body. In some embodiments, during the specification of the target region, the remote expert can select particular subset of key physical points in the target region of the patient's body as the target points for the treatment procedure. In some embodiments, the remote expert is also given a way to specify the order by which these target points are to be manipulated in the treatment procedure. In the treatment parameter region, the remote expert can specify the equipment needed (e.g., long needles) and the time required for each needle to remain inserted (e.g., 20 minutes). In this particular example, the acupuncture procedure has been started by the remote expert (e.g., as indicated by the "paused" button shown next to the first treatment procedure). If the remote expert wishes to stop the current treatment procedure before it is completed (e.g., due to patient's discomfort indicated by the sensor data), the remote expert can activate the pause button next to the first treatment procedure. The robot located at the local site will stop the treatment procedure according to the command received from the remote expert.

As illustrated in FIG. 5, in this example, the remote expert has started to specify a fourth treatment procedure (e.g., electric stimulation) in the treatment plan. The expert has selected a target region (e.g., region 4 (e.g., user's neck region)) of a virtualized version of the patient's body 522 shown in a target selection region 520. As shown in FIG. 5, the remote expert can select a posture for the treatment procedure from a listing of possible postures 525 (e.g., lying facing downward, lying with left leg slightly bent, lying on the left side with both legs slightly bent, etc.). In some embodiments, once the remote expert has selected a posture for the treatment procedure, the selected posture is shown in the target selection region 520 in an enlarged state. The key target points for the patient's body are displayed on the three-dimensional model shown in the target selection region. In some embodiments, the model shown in the target selection region 520 is the actual three-dimensional model generated from the patient's images. In some embodiments, the model shown in the target selection region is a template three dimensional model that best matches the patient's body. In some embodiments, the model shown in the target selection region is a fitted version of the three dimensional model that best matches the patient's body. The benefit of using a generic model is reduced computation and faster performance. The benefit of using templates that best match the patient's body is that the model more closely reflects the actual patient's condition (e.g., obese, weak with little fat under skin, etc.). In some embodiments, the posture of the model shown in target region selection region is adjustable in response to the remote expert's input. For example, the remote expert can drag the model's leg to bend it, or move the model's arm to raise it above the model's head, etc. In some embodiments, once the model's posture is adjusted, the adjusted model posture is sent to the local site, and the patient or local operator can help the patient to adjust the patient's posture accordingly before the corresponding treatment procedure is started.

In the target selection region 520, the key physical points 524 are shown overlaid on the model of the patient's body. The remote expert can select a region by placing a resizable box 526 over a region on the model. The remote expert can also select particular key physical points (e.g., point 528) within the selected target region to be the target points of the treatment procedure. Once all the target region is selected, the remote expert can select the "done" button in the target selection region to enter the information of the target region and target points into the target region portion of the treatment procedure 4 "electric stimulation." Once the expert has also selected the treatment parameters, e.g., electric current, etc. for the treatment procedure, a control is enabled (e.g., a start button is displayed) for starting the treatment procedure.

In some embodiments, the user interface 500 provides preset treatment plans for the remote expert to select for a particular patient. In some embodiments, the user interface 500 allows the remote expert to save the current treatment plan once it is fully specified or fully completed. In some embodiments, after a saved or preset treatment plan is selected, and the treatment procedures and corresponding parameters are populated in the treatment plan specification region, the remote expert can still modify particular aspects of the treatment plan, in the same manner as outlined above, using the user interface 500.

In some embodiments, requiring the patient to be still during the treatment and tracking and predicting user's movement based on the manipulation being applied, helps to reduce issues with network latency as well. In some embodiments, if too much movement is detected during a treatment procedure, an alert is generated on the user interface 500, and the remote expert can enter a command in the user interface 500 to request the treatment procedure to be performed again and require the robot to restrain the movement of the patient during the procedure.

FIG. 6 is a flowchart of a method 600 of providing remotely-guided physical treatment, in accordance with some embodiments. The method 600 is performed at a computing device (e.g., a central control server 136) having one or more processors and memory, wherein the computing device is (602) communicably coupled to a therapeutic robot (e.g., robot 128 collocated with the patient 104), and to a guidance device (e.g., computer collocated with the remote expert 110) including a first display generation component and a first input device (e.g., a haptic enabled input device, a touch screen, or a mouse), and wherein the therapeutic robot is collocated with a treatment subject (e.g., a patient 104) and the guidance device is collocated with a treatment guidance provider (e.g., a remote expert 110) during a physical treatment session.

In the method 600, the computing device receives (604) one or more full-body images of the treatment subject (e.g., the images are streamed to the central control server, the images including color images and corresponding depth data, the images are captured by an RGBD camera located at the local site of the patient during the treatment session). The computing device generates (606) a plurality of key physical points (e.g., pressure points, acupuncture points, sites of electric stimulation, trigger points, joints, etc.) for the treatment subject. To generate the plurality of key physical points, the computing device determines (608) a plurality of shape parameters and posture parameters of the treatment subject from the one or more full-body images of the treatment subject. The computing device further identifies (610) a first three-dimensional human body template that corresponds to the plurality of shape parameters and posture parameters of the treatment subject (e.g., based on the shape parameters and posture parameters of the patient in the streamed 3D images, the trained template model identifies the best matching three dimensional human body template from a large number of human body templates), wherein the first three-dimensional human body template has a corresponding set of key physical points (e.g., the locations of the key physical points are known with respect to each template known to the template model). The computing device then fits (612) the identified first three-dimensional human body template to the one or more full-body images of the treatment subject (e.g., the shape, size, posture of the patient's body images and the identified best matching human body template are not exactly the same, and the fitting is performed with an error or difference function being minimized as a result of the fitting), wherein the fitting causes adjustments to locations of at least one of the corresponding set of key physical points of the first three-dimensional human body template (e.g., when the three-dimensional human body template is fitted, the locations of the key physical points of the human body template move accordingly). The computing device provides (614) the adjusted locations of the corresponding set of key physical points of the first three-dimensional human body template to the guidance device, wherein the adjusted locations of the corresponding set of key physical points of the first three-dimensional human body template provides a basis (e.g., as shown in FIG. 5) for a treatment procedure that is specified by the treatment guidance provider during the physical treatment session.

In some embodiments, during performance of the treatment procedure on the treatment subject by the therapeutic robot: the computing device receives additional full-body images of the treatment subject; the computing device detects movement of the treatment subject made during the treatment procedure based on the additional full-body images of the treatment subject; and in response to detecting movement of the treatment subject made during the treatment procedure, the computing device re-fits the identified first three-dimensional human body template to the additional full-body images of the treatment subject (e.g., the shape, size, posture of the patient's body images and the identified best matching human body template are not exactly the same, and the fitting is performed with an error or difference function being minimized as a result of the fitting), wherein the re-fitting results in additional adjustments to locations of at least one of the corresponding set of key physical points of the first three-dimensional human body template (e.g., when the three-dimensional human body template is re-fitted, the locations of the key physical points of the human body template move accordingly). The computing device provides the additionally adjusted locations of the corresponding set of key physical points of the first three-dimensional human body template to the guidance device, wherein the additionally adjusted locations of the corresponding set of key physical points of the first three-dimensional human body template provides a modified basis for the treatment procedure that is performed during the treatment session. For example, the locations of key physical points are tracked during the treatment procedure and the robot's treatment actions are adjusted based on the changes in the locations of the key physical points when the patients shift his/her body during the treatment procedure.

In some embodiments, during performance of the treatment procedure on the treatment subject by the therapeutic robot: the computing device receives sensor data from a plurality of sensors collocated with the treatment subject (e.g., heart rate, blood pressure, perspiration, pressure/force on grab bar, etc.); the computing device correlates the sensor data based on time (e.g., for each point in time, a set of sensor data values are correlated); and the computing device automatically adjusts one or more treatment parameters (e.g., reducing electric current for electric stimulation, or reducing force/pressure for acupressure treatment, reducing needle depth for acupuncture treatment, etc.) in accordance with the correlated sensor data (e.g., correlated sensor data for the current time indicates that the patient is in stress, in too much pain, etc.). For example, the remote expert's treatment procedure may set the treatment parameters within an acceptable range (e.g., a range of electric current, a range of pressure/force, a range of needle depth, etc.), and the central control computer sends commands to the robot the adjust the treatment parameter values actually used in the performance of the treatment procedure in real-time based on the sensor feedback data received from the patient.

In some embodiments, after providing the adjusted locations of the corresponding set of key physical points of the first three-dimensional human body template to the guidance device, the computing device receives user input from the guidance device is collocated with a treatment guidance provider, wherein the user input further modifies the adjusted locations of the corresponding set of key physical points of the first three-dimensional human body template. For example, the remote expert may move the automatically generated key physical points on the virtualized model of the patient's body in accordance with his own expertise. The computing device provides a modified basis for the treatment procedure that is performed during the treatment session to the therapeutic robot, in accordance with the user input. For example, if the treatment procedure is to apply a needle to acupuncture point x on the patient's body, the automatically generated location for acupuncture point x is location 1 on the patient's body, and the remote expert has adjusted the location of acupuncture point x to location 2 on the patient's body, the therapeutic robot will insert the acupuncture needle at location 2 of the patient's body.

In some embodiments, the computing device detects a first movement input via the first input device, wherein a location of the first movement input corresponds to movement across a first surface portion of the treatment subject; the computing device performs haptic rendering of the first surface portion of the treatment subject in response to the first movement input; and the computing device provides haptic feedback to the treatment guidance provider via the first input device, wherein the haptic feedback constrains the first movement input in accordance with a contour of the first surface portion of the treatment subject, and wherein the haptic feedback simulates one or more surface characteristics of the first surface portion of the treatment subject. For example, when the remote expert uses a haptic input device to cause a virtual pointer to slide over the shoulder portion of the virtualized version of the patient's body, the movement of the virtual pointer is constrained to move on the surface of the shoulder (as opposed to penetrating the surface of the shoulder), and when the remote expert pushes against the shoulder using the haptic input device, the haptic feedback will include a reaction force that pushes against the user's hand, and the friction force will also increase when the remote expert pushes against the shoulder while dragging the virtual pointer. This haptic feedback allows the remote expert realistically experience the patient's shoulder, and/or demonstrate the massage actions to be performed on the patient's shoulder.

In some embodiments, during performance of the treatment procedure on the treatment subject by the therapeutic robot: the computing device receives a command from the guidance device to directly control the therapeutic robot; and in response to receiving the command from the guidance device, the computing device interrupts performance of the treatment procedure on the treatment subject by the therapeutic robot. For example, the remote expert may determine that a particular portion of the treatment procedure should be performed with more care, and interrupts the robot (e.g., by activating a pause button on the user interface 500), and then activates a teleoperation control to directly control the movement of the robot.

In some embodiments, after interrupting the performance of the treatment procedure on the treatment subject by the therapeutic robot: the computing device receives direct manipulation commands from the guidance device, including one or more movement inputs received from the first input device; and in response to receiving the direct manipulation commands from the guidance device, the computing device performs movements using the therapeutic robot in accordance with movement parameter and force parameters of the one or more movement inputs. For example, the remote expert can provide the movement inputs (e.g., massage motions) using the haptic enabled input device, with the location, amount of force, speed, and movement patterns suitable for the current treatment situation, and the same movement inputs are replicated by the therapeutic robot exactly (e.g., with the same location, force, speed, and movement patterns) on the patient's body.

It should be understood that the particular order in which the operations in method 600 have been described is merely an example and is not intended to indicate that the described order is the only order in which the operations could be performed. One of ordinary skill in the art would recognize various ways to reorder the operations described herein. Additionally, it should be noted that details of other processes described herein with respect to other methods described herein are also applicable in an analogous manner to method 600 described above with respect to FIG. 6. For brevity, these details are not repeated here.

The operations in the information processing methods described above are, optionally implemented by running one or more functional modules in information processing apparatus such as general purpose processors or application specific chips.

Figure 7:
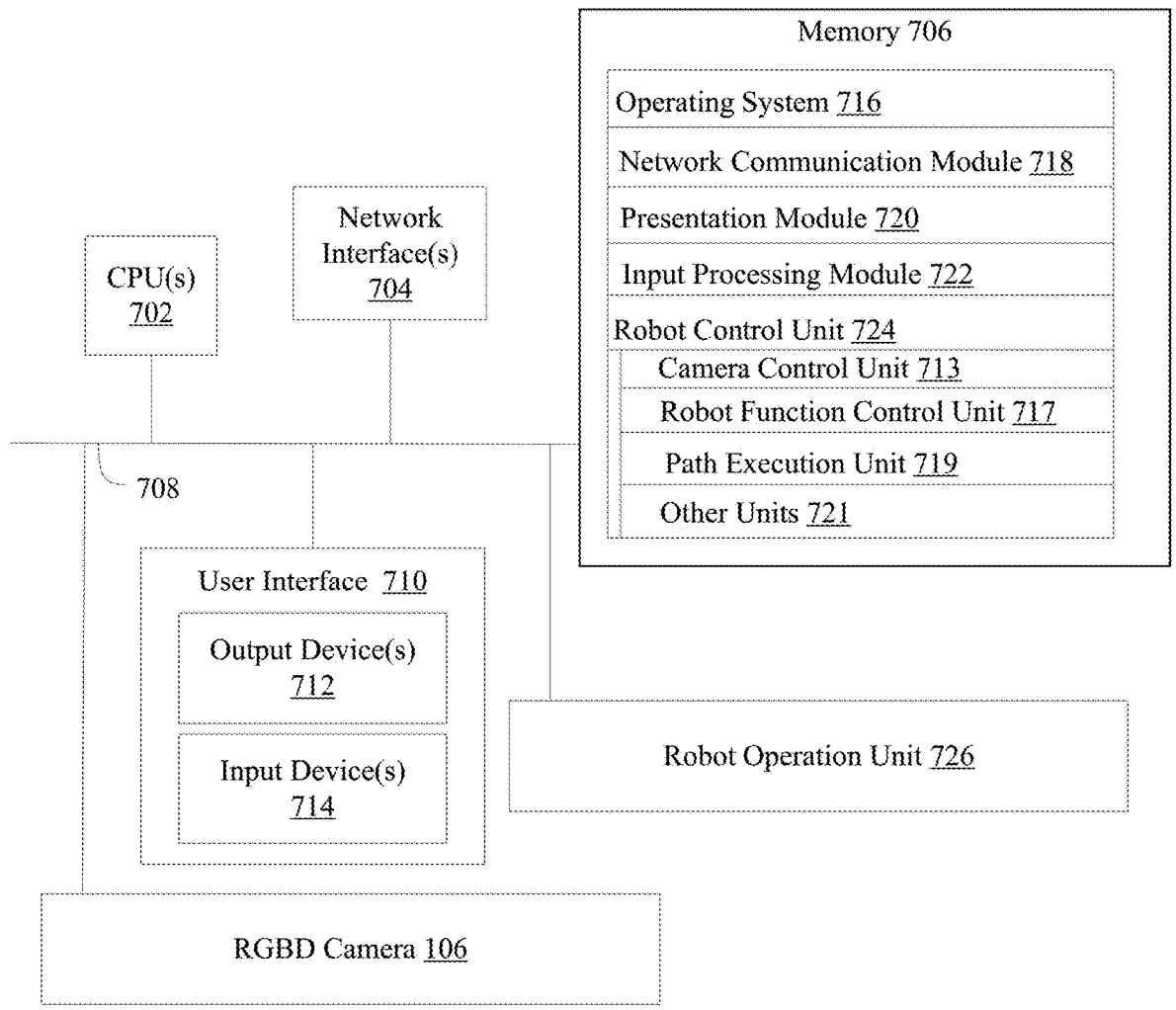
FIG. 7 is a block diagram illustrating an exemplary local site equipment (e.g., a robot) in accordance with some embodiments.

FIG. 7 is a block diagram illustrating local site equipment 700 including an exemplary robot 128 and local-site computing device 114 in accordance with some embodiments.

The local site equipment 700 includes one or more processing units (CPUs) 702, one or more network interfaces 704 (e.g., including the I/O interface to server 136), memory 706, and one or more communication buses 708 for interconnecting these components (sometimes called a chipset). The memory 706 includes high-speed random access memory, such as DRAM, SRAM, DDR RAM, or other random access solid state memory devices; and, optionally, includes non-volatile memory, such as one or more magnetic disk storage devices, one or more optical disk storage devices, one or more flash memory devices, or one or more other non-volatile solid state storage devices. The memory 706, optionally, includes one or more storage devices remotely located from the one or more processing units 702. The memory 706, or alternatively the non-volatile memory within the memory 706, includes a non-transitory computer readable storage medium. In some implementations, the memory 706, or the non-transitory computer readable storage medium of the memory 706, stores the following programs, modules, and data structures, or a subset or superset thereof:

Operating system 716 including procedures for handling various basic system services and for performing hardware dependent tasks;

Network communication module 718 for connecting the robot 128 to other computing devices;

Presentation module 720 for enabling presentation of information at the robot 128 via the one or more output devices 712 (e.g., displays, speakers, etc.) associated with the user interface 710;

Input processing module 722 for detecting one or more user inputs or interactions from one of the one or more input devices 714 and interpreting the detected input or interaction;

Control Unit 724 for controlling functions of the robot 128 and the local site equipment, including camera control unit 713 for controlling RGBD camera 106 of the robot 128, robot function control unit 717 for controlling the robot operation unit 726 of the robot, path execution unit 719 for executing a path in accordance with a high level instructions of a path planner, and other units for implementing the functions of the robot 128 as described herein.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, modules or data structures, and thus various subsets of these modules may be combined or otherwise re-arranged in various implementations. In some implementations, memory 706, optionally, stores a subset of the modules and data structures identified above. Furthermore, the memory 706, optionally, stores additional modules and data structures not described above.

In some implementations, at least some of the functions of the local-site equipment are performed by the server 136, and the corresponding sub-modules of these functions may be located within the server 136 rather than the local-site equipment. The local-site equipment shown in FIG. 7 is merely illustrative, and different configurations of the modules for implementing the functions described herein are possible in various implementations.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, or modules, and thus various subsets of these modules may be combined or otherwise re-arranged in various implementations. In some implementations, the memory 706, optionally, stores a subset of the modules and data structures identified above. Furthermore, the memory 706, optionally, stores additional modules and data structures not described above.

Figure 8:
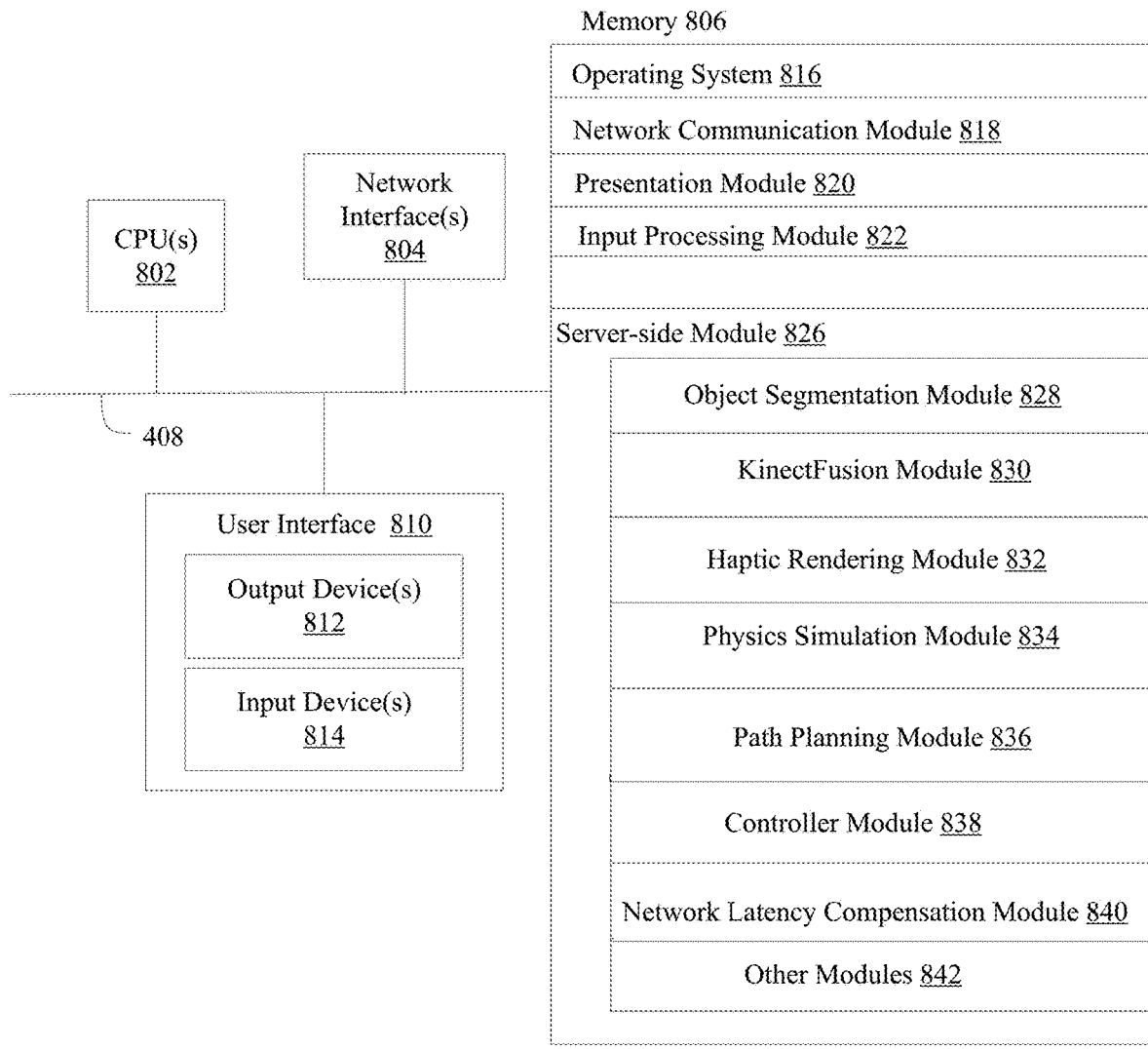
FIG. 8 is a block diagram illustrating an exemplary server in accordance with some implementations.

FIG. 8 is a block diagram illustrating an exemplary server 136 in accordance with some implementations. The server system 136, typically, includes one or more processing units (CPUs) 802, one or more network interfaces 804 (e.g., including the I/O interface to one or more robots 128 and the I/O interface to one or more user-side devices, such as local site equipment 700 and remote site equipment 900), memory 806, and one or more communication buses 808 for interconnecting these components (sometimes called a chipset). The memory 806 includes high-speed random access memory, such as DRAM, SRAM, DDR RAM, or other random access solid state memory devices; and, optionally, includes non-volatile memory, such as one or more magnetic disk storage devices, one or more optical disk storage devices, one or more flash memory devices, or one or more other non-volatile solid state storage devices. The memory 806, optionally, includes one or more storage devices remotely located from the one or more processing units 802. The memory 806, or alternatively the non-volatile memory within the memory 806, includes a non-transitory computer readable storage medium. In some implementations, the memory 806, or the non-transitory computer readable storage medium of the memory 806, stores the following programs, modules, and data structures, or a subset or superset thereof:

Operating system 816 including procedures for handling various basic system services and for performing hardware dependent tasks;

Network communication module 818 for connecting the server 136 to other computing devices (e.g., the local site equipment 700 (e.g., cameras and sensors, and computing devices) and the remote site equipment 900 (e.g., including input devices (e.g., device 111), display devices, and computing devices));

Presentation module 820 for enabling presentation of information at the server 136 via the one or more output devices 812 (e.g., displays, speakers, etc.) associated with the user interface 810;

Input processing module 822 for detecting one or more user inputs or interactions from one of the one or more input devices 814 and interpreting the detected input or interaction;

Server-side modules 826 for controlling functions of the server 136, including object segmentation module 828 for performing object segmentation in the virtualized environment, KinectFusion module 830 for generating and updating the virtualized environment based on the image and depth data stream received from the robot, Haptic rendering module 832 for generating haptic feedback based on the user's input provided via the haptic enabled input device and based on the location of the input in the virtualized environment, physics simulation module for generating reaction and friction force rendering as well as object interaction models in the virtualized environment, path planning module 836 for generating a planned path based on the virtualized environment and haptics markings and virtual objects present in the virtualized environment, controller module 838 for controlling path execution by the robot, network latency compensation module 840 for adjusting path planning based on network delays, and other modules 842 for implementing other functions (e.g., modules 138, 140, 142, 144, 146, 144, 146, 150, 152, 154, 156, and 158) of the server 136 as described herein.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, modules or data structures, and thus various subsets of these modules may be combined or otherwise re-arranged in various implementations. In some implementations, memory 806, optionally, stores a subset of the modules and data structures identified above. Furthermore, the memory 806, optionally, stores additional modules and data structures not described above.

In some implementations, at least some of the functions of the server 136 are performed by the robot 128, the local-site computing device 114, or the remote-site computing device 115, and the corresponding sub-modules of these functions may be located within the robot, the local-site computing device 114, or the remote-site computing device 115, rather than the server 136. The server 136 shown in FIG. 8 is merely illustrative, and different configurations of the modules for implementing the functions described herein are possible in various implementations.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, or modules, and thus various subsets of these modules may be combined or otherwise re-arranged in various implementations. In some implementations, the memory 806, optionally, stores a subset of the modules and data structures identified above. Furthermore, the memory 806, optionally, stores additional modules and data structures not described above.

Figure 9:
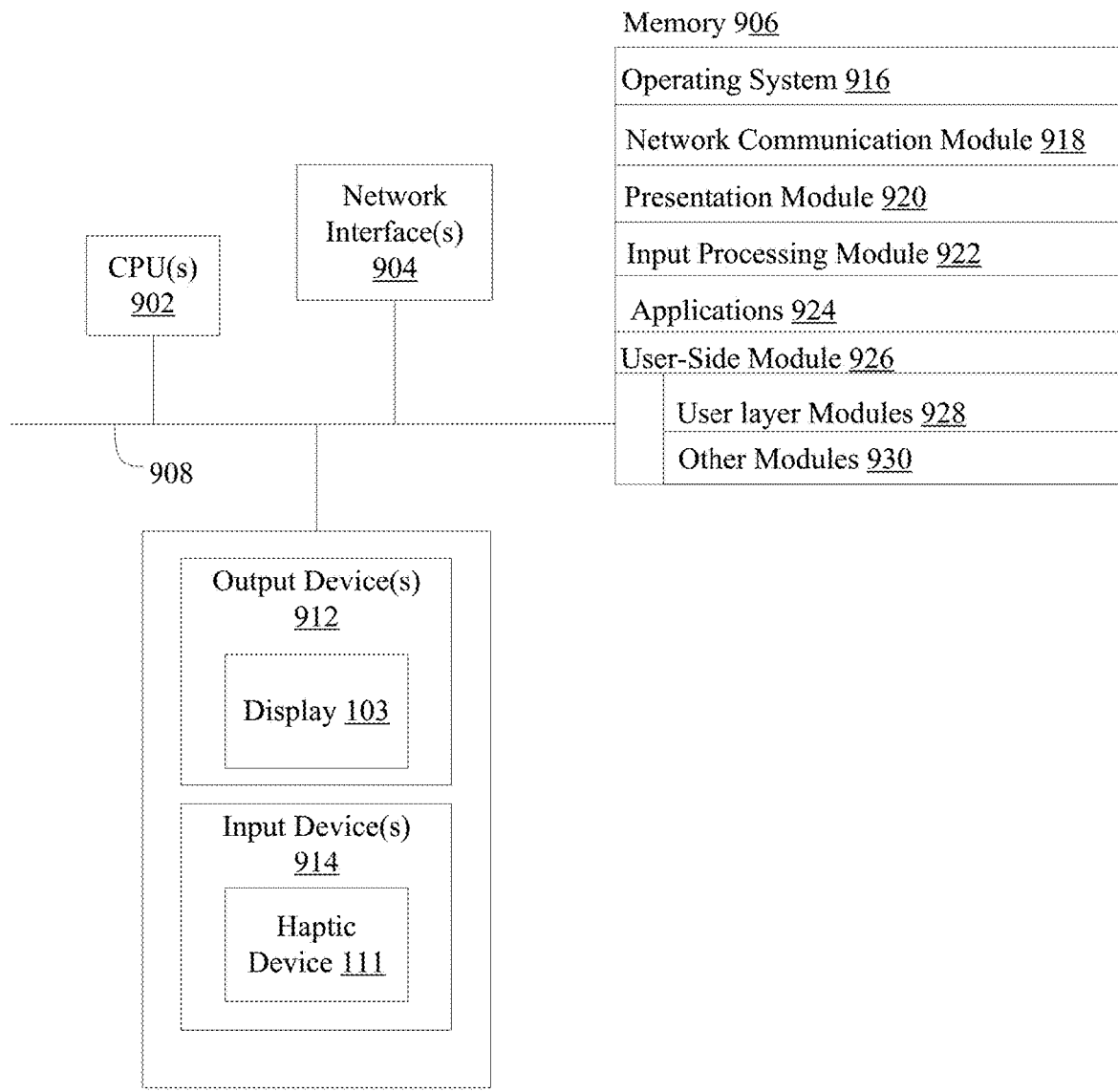
FIG. 9 is a block diagram illustrating an exemplary expert-side device in accordance with some implementations.

FIG. 9 is a block diagram illustrating an exemplary remote-site device 900 in accordance with some implementations. The remote site device 900, typically, includes one or more processing units (CPUs) 902, one or more network interfaces 904 (e.g., including the I/O interface to server 110), memory 906, and one or more communication buses 908 for interconnecting these components (sometimes called a chipset). The memory 906 includes high-speed random access memory, such as DRAM, SRAM, DDR RAM, or other random access solid state memory devices; and, optionally, includes non-volatile memory, such as one or more magnetic disk storage devices, one or more optical disk storage devices, one or more flash memory devices, or one or more other non-volatile solid state storage devices. The memory 906, optionally, includes one or more storage devices remotely located from the one or more processing units 902. The memory 906, or alternatively the non-volatile memory within the memory 906, includes a non-transitory computer readable storage medium. In some implementations, the memory 906, or the non-transitory computer readable storage medium of the memory 906, stores the following programs, modules, and data structures, or a subset or superset thereof:

Operating system 916 including procedures for handling various basic system services and for performing hardware dependent tasks;

Network communication module 918 for connecting the server 136 to other computing devices;

Presentation module 920 for enabling presentation of information at the remote-side device 900 via the one or more output devices 912 (e.g., displays 103, speakers, haptic-enabled input device 111, etc.) associated with the user interface 910;

Input processing module 922 for detecting one or more user inputs or interactions from one of the one or more input devices 914 (e.g., haptic-enabled input device 111) and interpreting the detected input or interaction;

Applications 924 for implementing various user-level functions, such as word processing, drawing, etc.

User-side modules 926 for controlling functions of the user-side devices, including user layer module 928 and other modules 930 for implementing other functions of the user-side device as described herein.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, modules or data structures, and thus various subsets of these modules may be combined or otherwise re-arranged in various implementations. In some implementations, memory 906, optionally, stores a subset of the modules and data structures identified above. Furthermore, the memory 906, optionally, stores additional modules and data structures not described above.

In some implementations, at least some of the functions of the server 136 are performed by the remote-site device 900, and the corresponding sub-modules of these functions may be located within the server rather than the remote-site device 900. The remote-site device 900 shown in FIG. 9 is merely illustrative, and different configurations of the modules for implementing the functions described herein are possible in various implementations.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, or modules, and thus various subsets of these modules may be combined or otherwise re-arranged in various implementations. In some implementations, the memory 906, optionally, stores a subset of the modules and data structures identified above. Furthermore, the memory 906, optionally, stores additional modules and data structures not described above.

What is claimed is:

1. A method, comprising:
at a computing device having one or more processors and memory, wherein the computing device is communicably coupled to a therapeutic robot:
  receiving one or more full-body images of a treatment subject;
  generating a plurality of key physical points for a treatment subject, including:
    determining a plurality of shape parameters and posture parameters of the treatment subject from the one or more full-body images of the treatment subject;
    identifying a first three-dimensional human body template that corresponds to the plurality of shape parameters and posture parameters of the treatment subject, wherein the first three-dimensional human body template has a corresponding set of key physical points; and
    fitting the identified first three-dimensional human body template to the one or more full-body images of the treatment subject, wherein the fitting causes adjustments to locations of at least one of the corresponding set of key physical points of the first three-dimensional human body template;
  providing the adjusted locations of the corresponding set of key physical points of the first three-dimensional human body template to a guidance device during a physical treatment session of the treatment subject; and
during performance of a treatment procedure on the treatment subject by the therapeutic robot:
  receiving sensor data from a plurality of sensors collocated with the treatment subject;
  correlating the sensor data based on time; and
  automatically adjusting one or more treatment parameters in accordance with the correlated sensor data.

2. The method of claim 1, including:
during performance of a treatment procedure on the treatment subject by the therapeutic robot:
  receiving additional full-body images of the treatment subject;
  detecting movement of the treatment subject made during the treatment procedure based on the additional full-body images of the treatment subject; and
  in response to detecting movement of the treatment subject made during the treatment procedure,
    re-fitting the identified first three-dimensional human body template to the additional full-body images of the treatment subject, wherein the re-fitting results in additional adjustments to locations of at least one of the corresponding set of key physical points of the first three-dimensional human body template; and
    providing the additionally adjusted locations of the corresponding set of key physical points of the first three-dimensional human body template to the guidance device during the treatment session.

3. The method of claim 1, including:
after providing the adjusted locations of the corresponding set of key physical points of the first three-dimensional human body template to the guidance device, receiving user input from the guidance device that is collocated with a treatment guidance provider, wherein the user input further modifies the adjusted locations of the corresponding set of key physical points of the first three-dimensional human body template; and
providing a modified basis for a treatment procedure that is performed during the treatment session to the therapeutic robot, in accordance with the user input.

4. The method of claim 1, including:
detecting a first movement input via a first input device, wherein a location of the first movement input corresponds to movement across a first surface portion of the treatment subject;
performing haptic rendering of the first surface portion of the treatment subject in response to the first movement input; and
providing haptic feedback to a treatment guidance provider via the first input device, wherein the haptic feedback constrains the first movement input in accordance with a contour of the first surface portion of the treatment subject, and wherein the haptic feedback simulates one or more surface characteristics of the first surface portion of the treatment subject.

5. The method of claim 1, including:
during performance of a treatment procedure on the treatment subject by the therapeutic robot:
receiving a command from the guidance device to directly control the therapeutic robot; and
in response to receiving the command from the guidance device, interrupting performance of the treatment procedure on the treatment subject by the therapeutic robot.

6. The method of claim 5, including:
after interrupting the performance of the treatment procedure on the treatment subject by the therapeutic robot:
receiving direct manipulation commands from the guidance device, including one or more movement inputs received from a first input device; and
in response to receiving the direct manipulation commands from the guidance device, performing movements using the therapeutic robot in accordance with movement parameter and force parameters of the one or more movement inputs.

7. A computing device, comprising:
one or more processors; and
memory storing instructions, wherein:
the computing device is communicably coupled to a therapeutic robot; and
the instructions, when executed by the one or more processors, cause the processors to perform operations comprising:
receiving one or more full-body images of the treatment subject;
generating a plurality of key physical points for a treatment subject, including:
determining a plurality of shape parameters and posture parameters of the treatment subject from the one or more full-body images of the treatment subject;
identifying a first three-dimensional human body template that corresponds to the plurality of shape parameters and posture parameters of the treatment subject, wherein the first three-dimensional human body template has a corresponding set of key physical points; and
fitting the identified first three-dimensional human body template to the one or more full-body images of the treatment subject, wherein the fitting causes adjustments to locations of at least one of the corresponding set of key physical points of the first three-dimensional human body template;
providing the adjusted locations of the corresponding set of key physical points of the first three-dimensional human body template to a guidance device during a physical treatment session of the treatment subject; and
during performance of a treatment procedure on the treatment subject by the therapeutic robot:
receiving sensor data from a plurality of sensors collocated with the treatment subject;
correlating the sensor data based on time; and
automatically adjusting one or more treatment parameters in accordance with the correlated sensor data.

8. The computing device of claim 7, wherein the operations include:
during performance of a treatment procedure on the treatment subject by the therapeutic robot:
receiving additional full-body images of the treatment subject;
detecting movement of the treatment subject made during the treatment procedure based on the additional full-body images of the treatment subject; and
in response to detecting movement of the treatment subject made during the treatment procedure:
re-fitting the identified first three-dimensional human body template to the additional full-body images of the treatment subject, wherein the re-fitting results in additional adjustments to locations of at least one of the corresponding set of key physical points of the first three-dimensional human body template; and
providing the additionally adjusted locations of the corresponding set of key physical points of the first three-dimensional human body template to the guidance device during the treatment session.

9. The computing device of claim 7, wherein the operations include:
after providing the adjusted locations of the corresponding set of key physical points of the first three-dimensional human body template to the guidance device, receiving user input from the guidance device that is collocated with a treatment guidance provider, wherein the user input further modifies the adjusted locations of the corresponding set of key physical points of the first three-dimensional human body template; and
providing a modified basis for a treatment procedure that is performed during the treatment session to the therapeutic robot, in accordance with the user input.

10. The computing device of claim 7, wherein the operations include:
detecting a first movement input via a first input device, wherein a location of the first movement input corresponds to movement across a first surface portion of the treatment subject;
performing haptic rendering of the first surface portion of the treatment subject in response to the first movement input; and
providing haptic feedback to a treatment guidance provider via the first input device, wherein the haptic feedback constrains the first movement input in accordance with a contour of the first surface portion of the treatment subject, and wherein the haptic feedback simulates one or more surface characteristics of the first surface portion of the treatment subject.

11. The computing device of claim 7, wherein the operations include:
during performance of a treatment procedure on the treatment subject by the therapeutic robot:
receiving a command from the guidance device to directly control the therapeutic robot; and
in response to receiving the command from the guidance device, interrupting performance of the treatment procedure on the treatment subject by the therapeutic robot.

12. The computing device of claim 11, wherein the operations include:
after interrupting the performance of the treatment procedure on the treatment subject by the therapeutic robot:
receiving direct manipulation commands from the guidance device, including one or more movement inputs received from a first input device; and
in response to receiving the direct manipulation commands from the guidance device, performing movements using the therapeutic robot in accordance with movement parameter and force parameters of the one or more movement inputs.

13. A computer-readable storage medium stores instructions, the instructions, when executed by one or more processors of a computing device, cause the computing device to perform operations, wherein:
the computing device is communicably coupled to a therapeutic robot; and
the operations comprise:
receiving one or more full-body images of the treatment subject;
generating a plurality of key physical points for a treatment subject, including:
determining a plurality of shape parameters and posture parameters of the treatment subject from the one or more full-body images of the treatment subject;
identifying a first three-dimensional human body template that corresponds to the plurality of shape parameters and posture parameters of the treatment subject, wherein the first three-dimensional human body template has a corresponding set of key physical points; and
fitting the identified first three-dimensional human body template to the one or more full-body images of the treatment subject, wherein the fitting causes adjustments to locations of at least one of the corresponding set of key physical points of the first three-dimensional human body template;
providing the adjusted locations of the corresponding set of key physical points of the first three-dimensional human body template to a guidance device during a physical treatment session of the treatment subject; and
during performance of a treatment procedure on the treatment subject by the therapeutic robot:
receiving sensor data from a plurality of sensors collocated with the treatment subject;
correlating the sensor data based on time; and
automatically adjusting one or more treatment parameters in accordance with the correlated sensor data.

14. The computer-readable storage medium of claim 13, wherein the operations include:
during performance of a treatment procedure on the treatment subject by the therapeutic robot:
receiving additional full-body images of the treatment subject;
detecting movement of the treatment subject made during the treatment procedure based on the additional full-body images of the treatment subject; and
in response to detecting movement of the treatment subject made during the treatment procedure,
re-fitting the identified first three-dimensional human body template to the additional full-body images of the treatment subject, wherein the re-fitting results in additional adjustments to locations of at least one of the corresponding set of key physical points of the first three-dimensional human body template; and
providing the additionally adjusted locations of the corresponding set of key physical points of the first three-dimensional human body template to the guidance device during the treatment session.

15. The computer-readable storage medium of claim 13, wherein the operations include:
after providing the adjusted locations of the corresponding set of key physical points of the first three-dimensional human body template to the guidance device, receiving user input from the guidance device that is collocated with a treatment guidance provider, wherein the user input further modifies the adjusted locations of the corresponding set of key physical points of the first three-dimensional human body template; and
providing a modified basis for a treatment procedure that is performed during the treatment session to the therapeutic robot, in accordance with the user input.

16. The computer-readable storage medium of claim 13, wherein the operations include:
detecting a first movement input via a first input device, wherein a location of the first movement input corresponds to movement across a first surface portion of the treatment subject;
performing haptic rendering of the first surface portion of the treatment subject in response to the first movement input; and
providing haptic feedback to a treatment guidance provider via the first input device, wherein the haptic feedback constrains the first movement input in accordance with a contour of the first surface portion of the treatment subject, and wherein the haptic feedback simulates one or more surface characteristics of the first surface portion of the treatment subject.

17. The computer-readable storage medium of claim 13, wherein the operations include:
during performance of a treatment procedure on the treatment subject by the therapeutic robot:
receiving a command from the guidance device to directly control the therapeutic robot;
in response to receiving the command from the guidance device, interrupting performance of the treatment procedure on the treatment subject by the therapeutic robot; and
after interrupting the performance of the treatment procedure on the treatment subject by the therapeutic robot:
receiving direct manipulation commands from the guidance device, including one or more movement inputs received from the first input device; and in response to receiving the direct manipulation commands from the guidance device, performing movements using the therapeutic robot in accordance with movement parameter and force parameters of the one or more movement inputs.

* * * * *